United States Patent
Yu et al.

(10) Patent No.: US 9,273,344 B2
(45) Date of Patent: Mar. 1, 2016

(54) INSTRUMENT FOR CASSETTE FOR SAMPLE PREPARATION

(71) Applicant: LUMINEX CORPORATION, Austin, TX (US)

(72) Inventors: Steve Jia Chang Yu, San Jose, CA (US); Jesus Ching, San Jose, CA (US); Phillip You Fai Lee, San Francisco, CA (US); David Hsiang Hu, Palo Alto, CA (US)

(73) Assignee: LUMINEX CORPORATION, Austin, TX (US)

( * ) Notice: Subject to any disclaimer, the term of this patent is extended or adjusted under 35 U.S.C. 154(b) by 0 days.

(21) Appl. No.: 14/525,976

(22) Filed: Oct. 28, 2014

(65) Prior Publication Data
US 2015/0050726 A1    Feb. 19, 2015

Related U.S. Application Data

(63) Continuation of application No. 13/459,469, filed on Apr. 30, 2012, now Pat. No. 8,900,877, which is a continuation of application No. 13/234,770, filed on Sep. 16, 2011, now Pat. No. 8,168,443, which is a (Continued)

(51) Int. Cl.
*G01N 35/00* (2006.01)
*G01N 35/02* (2006.01)
(Continued)

(52) U.S. Cl.
CPC .............. *C12Q 1/6806* (2013.01); *G01N 35/08* (2013.01); *B01L 3/502707* (2013.01); *B01L 2300/0609* (2013.01); *G01N 35/026* (2013.01); *G01N 35/04* (2013.01); *G01N 2035/00366* (2013.01); *G01N 2035/00544* (2013.01);
(Continued)

(58) Field of Classification Search
CPC .............. C12Q 1/6806; G01N 2035/00366; G01N 2035/00544; G01N 2035/00574; G01N 35/08; G01N 35/04; G01N 35/026; Y10S 436/807; Y10T 436/10; Y10T 436/11; Y10T 436/115831; Y10T 436/25
See application file for complete search history.

(56) References Cited

U.S. PATENT DOCUMENTS 3,607,094 A    9/1971    Beer .............................. 422/63
3,802,782 A    4/1974    Natelson ...................... 356/409
(Continued)

FOREIGN PATENT DOCUMENTS

CA    2626808    4/2007
DE    10319045    12/2004
(Continued)

OTHER PUBLICATIONS

Office Action, issued in Australian Application No. 2014201790, dated Apr. 23, 2015.
(Continued)

*Primary Examiner* — Lyle Alexander
*Assistant Examiner* — Jennifer Wecker
(74) *Attorney, Agent, or Firm* — Parker Highlander PLLC

(57) ABSTRACT

A parallel processing system for processing samples is described. In one embodiment, the parallel processing system includes an instrument interface parallel controller to control a tray motor driving system, a close-loop heater control and detection system, a magnetic particle transfer system, a reagent release system, a reagent pre-mix pumping system and a wash buffer pumping system.

15 Claims, 14 Drawing Sheets

Related U.S. Application Data continuation of application No. 13/044,109, filed on Mar. 9, 2011, now Pat. No. 8,029,746, which is a continuation of application No. 12/821,446, filed on Jun. 23, 2010, now Pat. No. 7,910,062, which is a continuation of application No. 12/005,860, filed on Dec. 27, 2007, now Pat. No. 7,754,148.

(60) Provisional application No. 60/882,150, filed on Dec. 27, 2006.

(51) Int. Cl.
    *G01N 35/04* (2006.01)
    *G01N 35/08* (2006.01)
    *C12Q 1/68* (2006.01)
    *B01L 3/00* (2006.01)

(52) U.S. Cl.
    CPC ............... *G01N 2035/00574* (2013.01); *G01N 2035/00801* (2013.01); *G01N 2035/0412* (2013.01); *G01N 2035/0415* (2013.01); *Y10S 436/807* (2013.01); *Y10T 436/10* (2015.01); *Y10T 436/11* (2015.01); *Y10T 436/113332* (2015.01); *Y10T 436/115831* (2015.01); *Y10T 436/25* (2015.01)

(56) References Cited

U.S. PATENT DOCUMENTS

| | | | |
|---|---|---|---|
| 4,004,150 A | 1/1977 | Natelson | 250/328 |
| 4,201,578 A | 5/1980 | Abbott | 430/222 |
| 4,439,039 A | 3/1984 | Suovaniemi | 356/416 |
| 4,448,534 A | 5/1984 | Wetz et al. | 356/435 |
| 4,495,149 A | 1/1985 | Iwata et al. | 422/65 |
| 4,626,684 A | 12/1986 | Landa | 250/328 |
| 4,762,420 A | 8/1988 | Bowley | 356/436 |
| 5,035,505 A | 7/1991 | Tsukada et al. | 356/319 |
| 5,073,029 A | 12/1991 | Eberly et al. | 356/432 |
| 5,139,745 A | 8/1992 | Barr et al. | 422/82.05 |
| 5,188,455 A | 2/1993 | Hammerstedt | 366/177.1 |
| 5,229,297 A | 7/1993 | Schnipelsky et al. | 436/94 |
| 5,234,665 A | 8/1993 | Ohta et al. | 422/73 |
| 5,242,660 A | 9/1993 | Hsei | 422/548 |
| 5,242,837 A | 9/1993 | Slovacek et al. | 436/536 |
| 5,283,624 A | 2/1994 | Tsukada et al. | 356/319 |
| 5,290,513 A | 3/1994 | Berthold et al. | 422/52 |
| 5,307,144 A | 4/1994 | Hiroshi et al. | 356/244 |
| 5,333,675 A | 8/1994 | Mullis et al. | 165/268 |
| 5,348,853 A | 9/1994 | Wang et al. | 435/6.12 |
| 5,389,524 A | 2/1995 | Larsen et al. | 435/29 |
| 5,397,709 A | 3/1995 | Berndt | 436/34 |
| 5,411,876 A | 5/1995 | Bloch et al. | 435/91.2 |
| 5,415,839 A | 5/1995 | Zaun et al. | 422/64 |
| 5,436,718 A | 7/1995 | Fernandes et al. | 356/73 |
| 5,475,610 A | 12/1995 | Atwood et al. | 700/269 |
| 5,494,646 A | 2/1996 | Seymour | 422/401 |
| 5,508,197 A | 4/1996 | Hansen et al. | 435/285.1 |
| 5,525,300 A | 6/1996 | Danssaert et al. | 422/552 |
| 5,525,466 A | 6/1996 | Slovacek et al. | 435/6.11 |
| 5,538,849 A | 7/1996 | Uematsu et al. | 435/6.19 |
| 5,541,072 A | 7/1996 | Wang et al. | 435/7.21 |
| 5,576,197 A | 11/1996 | Arnold | 435/91.2 |
| 5,578,818 A | 11/1996 | Kain et al. | 250/234 |
| 5,580,523 A | 12/1996 | Bard | 422/50 |
| 5,585,242 A | 12/1996 | Bouma et al. | 435/6.12 |
| 5,589,136 A | 12/1996 | Northrup et al. | 422/129 |
| 5,616,301 A | 4/1997 | Moser et al. | 422/64 |
| 5,627,041 A | 5/1997 | Shartle | 435/7.24 |
| 5,639,423 A | 6/1997 | Northrup et al. | 422/50 |
| 5,645,801 A | 7/1997 | Bouma et al. | 422/68.1 |
| 5,656,493 A | 8/1997 | Mullis et al. | 435/286.1 |
| 5,657,118 A | 8/1997 | Lee | 356/246 |
| 5,661,301 A | 8/1997 | Weiss | 850/26 |
| 5,665,975 A | 9/1997 | Kedar | 250/573 |
| 5,674,743 A | 10/1997 | Ulmer | 435/287.2 |
| 5,686,300 A | 11/1997 | Berndt | 435/287.5 |
| 5,705,628 A | 1/1998 | Hawkins | 536/254 |
| 5,738,825 A | 4/1998 | Rudigier et al. | 422/82.11 |
| 5,746,978 A | 5/1998 | Bienhaus et al. | 422/68.1 |
| 5,759,784 A | 6/1998 | Asp et al. | 435/6.12 |
| 5,811,312 A | 9/1998 | Hasegawa et al. | 436/527 |
| 5,825,478 A | 10/1998 | Wilcox et al. | 356/73 |
| 5,827,480 A | 10/1998 | Haff et al. | 422/68.1 |
| 5,837,144 A | 11/1998 | Bienhaus et al. | 210/695 |
| 5,861,124 A | 1/1999 | Hosoi et al. | 422/82.08 |
| 5,863,801 A | 1/1999 | Southgate et al. | 436/63 |
| 5,882,903 A | 3/1999 | Andrevski et al. | 435/91.2 |
| 5,897,783 A | 4/1999 | Howe et al. | 210/695 |
| 5,904,899 A * | 5/1999 | Hayashi | G01N 33/5302 422/560 |
| 5,935,522 A | 8/1999 | Swerdlow et al. | 422/70 |
| 5,989,499 A | 11/1999 | Catanzariti et al. | 422/63 |
| 6,004,512 A | 12/1999 | Titcomb et al. | 422/63 |
| 6,015,674 A | 1/2000 | Woudenber et al. | 435/6.12 |
| 6,027,945 A | 2/2000 | Smith et al. | 436/526 |
| 6,043,506 A | 3/2000 | Heffelfinger et al. | 250/584 |
| 6,050,719 A | 4/2000 | Winkler et al. | 366/144 |
| 6,057,163 A | 5/2000 | McMillian | 436/172 |
| 6,061,128 A | 5/2000 | Zweig et al. | 356/243.4 |
| 6,071,748 A | 6/2000 | Modlin et al. | 436/174 |
| 6,096,272 A | 8/2000 | Clark et al. | 422/64 |
| 6,211,989 B1 | 4/2001 | Wulf et al. | 359/210.1 |
| 6,222,619 B1 | 4/2001 | Herron et al. | 356/39 |
| 6,228,634 B1 | 5/2001 | Blumenfeld et al. | 435/286.1 |
| 6,232,608 B1 | 5/2001 | Giebeler et al. | 250/458.1 |
| 6,281,008 B1 | 8/2001 | Komai et al. | 435/306.1 |
| 6,296,810 B1 | 10/2001 | Ulmer | 422/82.07 |
| 6,297,018 B1 | 10/2001 | French et al. | 435/5 |
| 6,353,475 B1 | 3/2002 | Jensen et al. | 356/244 |
| 6,358,387 B1 | 3/2002 | Kopf-Sill et al. | 204/603 |
| 6,369,893 B1 | 4/2002 | Christel et al. | 356/417 |
| 6,429,007 B1 | 8/2002 | Kluttz et al. | 435/286.5 |
| 6,431,476 B1 | 8/2002 | Taylor et al. | 241/1 |
| 6,440,725 B1 | 8/2002 | Pourahmadi et al. | 435/288.5 |
| 6,451,258 B1 | 9/2002 | Malmqvist | 422/417 |
| 6,468,810 B1 | 10/2002 | Korpela | 436/526 |
| 6,492,162 B1 | 12/2002 | Sakurai et al. | 435/285.1 |
| 6,517,778 B1 | 2/2003 | Kumar et al. | 422/82.05 |
| 6,520,197 B2 | 2/2003 | Deshmukh et al. | 137/3 |
| 6,545,758 B1 | 4/2003 | Sandstrom | 356/317 |
| 6,565,815 B1 | 5/2003 | Chang et al. | 422/198 |
| 6,569,631 B1 | 5/2003 | Pantoliano et al. | 506/9 |
| 6,576,459 B2 | 6/2003 | Miles et al. | 435/286.5 |
| 6,597,450 B1 | 7/2003 | Andrews et al. | 356/317 |
| 6,645,758 B1 | 11/2003 | Schnipelsky et al. | 435/287.2 |
| 6,657,169 B2 | 12/2003 | Brown | 219/476 |
| 6,672,458 B2 | 1/2004 | Hansen et al. | 209/224 |
| 6,699,713 B2 | 3/2004 | Benett et al. | 435/287.2 |
| 6,730,501 B2 | 5/2004 | Eyre et al. | 435/91.2 |
| 6,730,883 B2 | 5/2004 | Brown et al. | 219/428 |
| 6,739,531 B2 | 5/2004 | Taylor | 241/1 |
| 6,764,859 B1 | 7/2004 | Kreuwel et al. | 436/178 |
| 6,783,934 B1 | 8/2004 | McMillan et al. | 435/6.11 |
| 6,787,338 B2 | 9/2004 | Wittwer et al. | 435/91.2 |
| 6,814,934 B1 | 11/2004 | Higuchi | 422/82.08 |
| 6,818,185 B1 | 11/2004 | Petersen et al. | 422/547 |
| 6,838,680 B2 | 1/2005 | Maher et al. | 250/458.1 |
| 6,852,284 B1 | 2/2005 | Holl et al. | 422/68.1 |
| 6,875,602 B2 | 4/2005 | Gutierrez | 435/286.2 |
| 6,890,742 B2 | 5/2005 | Ammann et al. | 435/91.2 |
| 6,893,879 B2 | 5/2005 | Petersen et al. | 436/178 |
| 6,908,759 B2 | 6/2005 | Jang | 435/285.1 |
| 6,927,852 B2 | 8/2005 | Reel | 356/317 |
| 6,955,589 B2 | 10/2005 | Kordonski et al. | 451/60 |
| 6,982,431 B2 | 1/2006 | Modlin et al. | 250/573 |
| 6,986,848 B2 | 1/2006 | Ikeda et al. | 210/695 |
| 7,008,789 B2 | 3/2006 | Gambini et al. | 435/287.2 |
| 7,027,683 B2 | 4/2006 | O'Connor et al. | 385/19 |
| 7,078,224 B1 | 7/2006 | Bitner et al. | 435/270 |
| 7,108,472 B2 * | 9/2006 | Norris | G01N 35/00029 414/222.07 |
| 7,148,043 B2 | 12/2006 | Kordunsky et al. | 435/91.2 |
| 7,171,863 B2 | 2/2007 | Tamura et al. | 73/864.14 |

(56) References Cited

U.S. PATENT DOCUMENTS

| | | | |
|---|---|---|---|
| 7,223,949 B2 | 5/2007 | Deka et al. | 219/548 |
| 7,236,237 B2 | 6/2007 | Schmilovitch et al. | 356/73 |
| 7,284,900 B2 | 10/2007 | Mayer | 366/197 |
| 7,294,466 B2 | 11/2007 | McMillan | 435/6.12 |
| 7,301,628 B2 | 11/2007 | Cunningham et al. | 356/326 |
| 7,329,488 B2 | 2/2008 | Roh et al. | 435/6.19 |
| 7,341,691 B2 | 3/2008 | Tamura et al. | 422/64 |
| 7,344,894 B2 | 3/2008 | Greenstein et al. | 436/518 |
| 7,358,078 B2 | 4/2008 | Chen et al. | 435/286.5 |
| 7,373,253 B2 | 5/2008 | Eyre | 702/19 |
| 7,387,891 B2 | 6/2008 | Boege et al. | 435/288.7 |
| 7,394,547 B2 | 7/2008 | Tan et al. | 356/480 |
| 7,423,750 B2 | 9/2008 | Hoshizaki et al. | 356/317 |
| 7,459,302 B2 | 12/2008 | Reid et al. | 435/286.1 |
| 7,498,164 B2 | 3/2009 | Oldham et al. | 435/288.7 |
| 7,507,575 B2 | 3/2009 | Bedingham et al. | 435/287.2 |
| 7,521,179 B2 | 4/2009 | Bachi | 435/6.1 |
| 7,584,019 B2 | 9/2009 | Feingold et al. | 700/245 |
| 7,585,663 B2 | 9/2009 | Shigeura et al. | 435/287.2 |
| 7,682,565 B2 | 3/2010 | Linton et al. | 422/68.1 |
| 7,699,979 B2 | 4/2010 | Li et al. | 210/138 |
| 7,718,072 B2 | 5/2010 | Safar et al. | 210/695 |
| 7,718,421 B2 | 5/2010 | Chen et al. | 435/288.5 |
| 7,727,473 B2 | 6/2010 | Ching et al. | 422/68.1 |
| 7,754,148 B2 | 7/2010 | Yu et al. | 422/65 |
| 7,910,062 B2 | 3/2011 | Yu et al. | 422/65 |
| 8,048,386 B2 | 11/2011 | Dority et al. | 422/500 |
| 8,124,024 B2 | 2/2012 | Ching et al. | 422/417 |
| 8,133,703 B2 | 3/2012 | Ching et al. | 435/91.2 |
| 8,168,443 B2 | 5/2012 | Yu et al. | 436/174 |
| 8,372,340 B2 | 2/2013 | Bird et al. | 422/64 |
| 2001/0036672 A1 | 11/2001 | Anderson et al. | 436/180 |
| 2003/0016352 A1 | 1/2003 | Goldman et al. | 356/317 |
| 2003/0073110 A1 | 4/2003 | Aritomi et al. | 435/6.12 |
| 2003/0129739 A1 | 7/2003 | Jones | 435/287.2 |
| 2003/0170686 A1 | 9/2003 | Hoet et al. | 435/6.12 |
| 2003/0203491 A1 | 10/2003 | Andrevski et al. | 436/46 |
| 2003/0224436 A1 | 12/2003 | Nelson et al. | 435/6.12 |
| 2004/0126783 A1 | 7/2004 | Bortolin et al. | 435/6.12 |
| 2004/0161788 A1 | 8/2004 | Chen et al. | 435/6.11 |
| 2004/0200909 A1 | 10/2004 | McMillan et al. | 241/1 |
| 2004/0209266 A1 | 10/2004 | Squirrell | 435/6.11 |
| 2004/0222395 A1 | 11/2004 | Yee | 251/65 |
| 2004/0259237 A1 | 12/2004 | Kellogg et al. | 435/287.1 |
| 2005/0194316 A1 | 9/2005 | Pourahmadi et al. | 210/634 |
| 2005/0244837 A1 | 11/2005 | McMillan et al. | 435/6.12 |
| 2006/0011539 A1 | 1/2006 | Lee et al. | 210/613 |
| 2006/0013725 A1 | 1/2006 | Larsen | 422/400 |
| 2006/0019379 A1 | 1/2006 | Taylor et al. | 435/306.1 |
| 2006/0030038 A1 | 2/2006 | Taylor et al. | 435/306.1 |
| 2006/0194264 A1 | 8/2006 | Sheppard et al. | 435/7.9 |
| 2006/0205085 A1 | 9/2006 | Handique et al. | 436/177 |
| 2006/0222569 A1 | 10/2006 | Barten et al. | 422/400 |
| 2006/0246490 A1 | 11/2006 | Anderson et al. | 435/6.11 |
| 2006/0257991 A1 | 11/2006 | McDevitt et al. | 435/287.2 |
| 2006/0269922 A1 | 11/2006 | Sagner et al. | 435/6.18 |
| 2006/0276972 A1 | 12/2006 | Light et al. | 702/19 |
| 2006/0292032 A1 | 12/2006 | Hataoka et al. | 422/552 |
| 2007/0036026 A1 | 2/2007 | Laibinis et al. | 366/273 |
| 2007/0054293 A1 | 3/2007 | Liu et al. | 435/287.2 |
| 2007/0054349 A1 | 3/2007 | Hickey | 435/32 |
| 2007/0077646 A1 | 4/2007 | Okamoto | 435/288.4 |
| 2007/0087431 A1 | 4/2007 | Ching et al. | 435/287.2 |
| 2007/0099289 A1 | 5/2007 | Irimia et al. | 435/287.2 |
| 2007/0125942 A1 | 6/2007 | Kido | 250/284 |
| 2007/0212698 A1 | 9/2007 | Bendele et al. | 435/6.16 |
| 2007/0248958 A1 | 10/2007 | Jovanovich et al. | 435/6.19 |
| 2007/0281288 A1 | 12/2007 | Belkin et al. | 435/4 |
| 2007/0292858 A1 | 12/2007 | Chen et al. | 435/6.18 |
| 2008/0003649 A1 | 1/2008 | Maltezos et al. | 435/91.2 |
| 2008/0050781 A1 | 2/2008 | Oldham et al. | 435/91.2 |
| 2008/0153096 A1 | 6/2008 | Witty et al. | 435/6.12 |
| 2008/0159915 A1 | 7/2008 | Yu et al. | 422/68.1 |
| 2008/0262213 A1 | 10/2008 | Wu et al. | 536/25.4 |
| 2008/0280285 A1 | 11/2008 | Chen et al. | 435/5 |
| 2008/0316482 A1 | 12/2008 | Hoshizaki et al. | 356/317 |
| 2009/0023201 A1 | 1/2009 | Hongo et al. | 435/287.2 |
| 2009/0030038 A1 | 1/2009 | Chu et al. | 514/312 |
| 2009/0130766 A1 | 5/2009 | Weekamp | 436/63 |
| 2009/0142745 A1 | 6/2009 | Breidenthal et al. | 435/3 |
| 2009/0155838 A1 | 6/2009 | Hale | 435/29 |
| 2009/0186344 A1 | 7/2009 | Farinas | 435/6.11 |
| 2009/0186357 A1 | 7/2009 | Mauk et al. | 435/6.15 |
| 2009/0215124 A1 | 8/2009 | Cao et al. | 435/91.2 |
| 2009/0269841 A1 | 10/2009 | Wojciechowski et al. | 435/325 |
| 2009/0291507 A1 | 11/2009 | Clemmens et al. | 436/501 |
| 2010/0112567 A1 | 5/2010 | Adolfsen et al. | 435/6.16 |
| 2010/0239471 A1 | 9/2010 | Ching et al. | 422/186.01 |
| 2011/0008907 A1 | 1/2011 | Patno et al. | 436/174 |
| 2011/0158849 A1 | 6/2011 | Yu et al. | 422/63 |
| 2011/0236960 A1 | 9/2011 | Bird et al. | 435/283.1 |
| 2012/0003631 A1 | 1/2012 | Yu et al. | 435/6.1 |

FOREIGN PATENT DOCUMENTS

| | | |
|---|---|---|
| JP | 11-271227 | 5/1999 |
| JP | 2001-108684 | 4/2001 |
| JP | 2009-512447 | 3/2009 |
| JP | 2010-505108 | 2/2010 |
| WO | WO 01/13096 | 2/2001 |
| WO | WO 2004/005553 | 1/2004 |
| WO | WO 2004/080597 | 9/2004 |
| WO | WO 2006/071770 | 7/2006 |
| WO | WO 2008/037995 | 4/2008 |
| WO | WO 2009/105711 | 8/2009 |

OTHER PUBLICATIONS

Office Action, issued in Canadian Application No. 2,796,586, dated Mar. 31, 2015.
Extended Search Report and Opinion, issued in European Application No. 06817150.3, dated May 28, 2014.
Extended Search Report and Opinion, issued in European Application No. 11747970.9, dated May 28, 2014.
Extended Search Report and Opinion, issued in European Application No. 12779471.7, dated May 28, 2014.
International Search Report and Written Opinion issued in PCT Application No. PCT/US2006/40835, mailed Dec. 4, 2007.
International Search Report and Written Opinion issued in PCT Application No. PCT/US2011/25871, mailed May 5, 2011.
Office Action, issued in Australian Application No. 2006304623, dated Apr. 21, 2011.
Office Action, issued in Australian Application No. 2006304623, dated Sep. 9, 2013.
Office Action, issued in Canadian Application No. 2,626,808, dated Apr. 12, 2013.
Office Action, issued in Canadian Application No. 2,626,808, dated Jan. 10, 2014.
Office Action, issued in Canadian Application No. 2,626,808, dated Sep. 11, 2014.
Office Action, issued in Chinese Application No. 200680043554.3, dated Mar. 30, 2011 (English Translation).
Office Action, issued, in Chinese Application No. 201310061818.X, dated Jun. 16, 2014 (English Translation).
Office Action issued in Japanese Patent Application No. 2008-536791, mailed Oct. 3, 2011.
Office Action, issued in Japanese Application No. 2008-536791, dated Jul. 17, 2012 (English Translation).
Office Action, issued in Korean Application No. 10-2008-7011947, dated May 22, 2013 (English Translation).
Office Action, issued in Korean Application No. 10-2013-7019433, dated Oct. 21, 2013 (English Translation).
Office Action, issued in Mexican Application No. MX/a/2008/005115, dated Sep. 7, 2010 (English Translation).
Office Action, issued in U.S. Appl. No. 12/789,831, dated Nov. 23, 2010.
Office Action, issued in U.S. Appl. No. 12/789,831, dated May 27, 2011.
Office Action, issued in U.S. Appl. No. 13/357,947, dated Oct. 5, 2012.

(56) References Cited

OTHER PUBLICATIONS

Office Action, issued in U.S. Appl. No. 13/910,953, dated Dec. 5, 2013.
Office Action, issued in U.S. Appl. No. 13/910,953, dated Mar. 28, 2014.
Office Action, issued in U.S. Appl. No. 12/005,860, dated Nov. 3, 2009.
Office Action, issued in U.S. Appl. No. 12/821,446, dated Sep. 1, 2010.
Office Action, issued in U.S. Appl. No. 13/459,469, dated May 15, 2013.
Office Action, issued in U.S. Appl. No. 13/459,469, dated Oct. 25, 2013.
Office Action, issued in U.S. Appl. No. 13/459,469, dated Mar. 28, 2014.
Office Action, issued in Australian Application No. 2011220873, dated Aug. 12, 2013.
Office Action, issued in Chinese Application No. 201180018623.6, dated Dec. 26, 2013.
Office Action, issued in Chinese Application No. 201180018623.6, dated Jul. 15, 2014.
Office Action, issued in U.S. Appl. No. 13/759,557, dated May 29, 2014.
Office Action, issued in U.S. Appl. No. 13/759,557, dated Sep. 3, 2014.
Office Action, issued in Japanese Application No. 2012-555102, dated Feb. 24, 2015.
Office Action, issued in European Application No. 12 779 471.7, dated Apr. 9, 2015.
Pilosof and Nieman, "Microporous membrance flow cell with nonimmobilized enzyme for chemiluminescent determination of glucose," *Anal. Chem.*, 54:1698-1701, 1982.

\* cited by examiner

INSTRUMENT FOR CASSETTE FOR SAMPLE PREPARATION

CROSS-REFERENCES TO RELATED APPLICATIONS

This application is continuation of U.S. patent application Ser. No. 13/459,469 (U.S. Pat. No. 8,900,877), entitled "Instrument for Cassette for Sample Preparation," filed Apr. 30, 2012, which is a continuation of U.S. patent application Ser. No. 13/234,7701 nm U.S. Pat. No. 8,168,443), entitled "Instrument for Cassette for Sample Preparation," filed Sep. 16, 2011, which is a continuation of U.S. patent application Ser. No. 13/044,109 (now U.S. Pat. No. 8,029,746), entitled "Instrument for Cassette for Sample Preparation," filed Mar. 9, 2011, which is a continuation of U.S. patent application Ser. No. 12/821,446 (now U.S. Pat. No. 7,910,062), entitled "Instrument for Cassette for Sample Preparation," filed Jun. 23, 2010, which is a continuation of U.S. patent application Ser. No. 12/005,860 (now U.S. Pat. No. 7,754,148), entitled "Instrument for Cassette for Sample Preparation," filed Dec. 27, 2007, which claims priority to U.S. Provisional Application Ser. No. 60/882,150, entitled "Instrument for Cassette for Sample Preparation," filed Dec. 27, 2006, each of which is incorporated herein by reference in its entirety.

FIELD

The present invention relates to the field of biotechnology devices and, in particular, to devices and methods for preparing samples.

BACKGROUND

DNA can be used to develop new drugs or to link someone to a crime. However, before this can be done, the DNA must be isolated from a sample. These samples include, for example, blood, urine, human cells, hair, bacteria, yeast and tissue. Each of these samples include cells, which include nucleic acid. Nucleic acid is a nucleotide chain, which conveys genetic information. The most common forms of nucleic acid are DNA and RNA.

In order to isolate the nucleic acid from the samples, prior art devices use a tray having several exposed cavities. The sample is placed into one of the cavities and conventional processing steps are used to isolate the DNA from the sample.

This prior art system has several disadvantages, including contamination, and inability to perform parallel processing or asynchronous processing. Since the cavities are exposed, contaminants can easily affect the DNA. In addition, the prior art system requires the preparation of several sampler at one time. In addition, these prior art systems require a significant amount of time to process multiple samples.

SUMMARY

In one embodiment, the present invention relates to on instrument for preparing samples. The instrument includes, for example, a parallel tray motor driving system; a close-loop heater control and detection system; a parallel magnetic particle transfer system; a parallel reagent release system; a reagent parallel pre-mix pumping system; a parallel wash buffer pumping system; and an instrument interlace controller to control the biological sample processing instrument that includes the parallel tray motor driving system, the close-loop heater control and detection system, the parallel magnetic particle transfer system, the parallel reagent release system, the parallel reagent pre-mix pumping system, and the parallel wash buffer pumping system.

In another embodiment, the present invention relates to a system for preparing samples. The system includes, for example, an enclosure; a parallel tray motor driving system in the enclosure to insert one or more magazines which contain one or more cassettes into the enclosure, the cassette having a sample therein; a close-loop heater control and detection system in the enclosure; a parallel magnetic particle transfer system in the enclosure; a parallel reagent release system in the enclosure; a parallel reagent pre-mix pumping system in the enclosure; and a parallel wash buffer pumping system in the enclosure.

BRIEF DESCRIPTION OF THE DRAWINGS

The invention is described by way of example with reference to the accompanying drawings, wherein:

FIG. 8 is a detailed perspective view of the reagent release and pre-mix assembly module in accordance with one embodiment of the invention;

DETAILED DESCRIPTION

Figure 1:
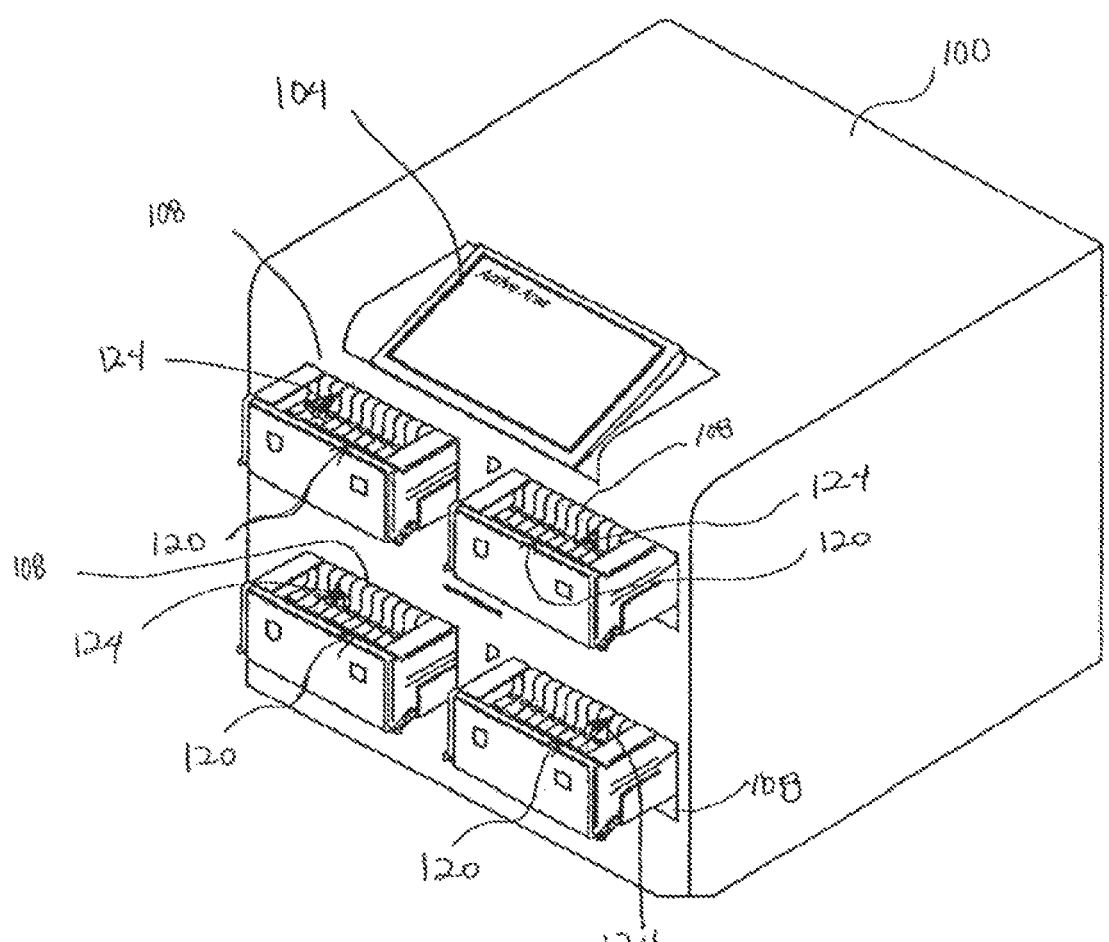
FIG. 1 is a perspective view of an instrument for a cassette for sample preparation in accordance with one embodiment of the invention.

FIG. 1 illustrates an instrument 100 in accordance with one embodiment of the invention. In one embodiment, the instrument 100 is a parallel processing system.

The illustrated instrument 100 includes a display 104 and openings 108. The openings 108 are configured to receive magazines 120. The magazines 120 each contain a series of cassettes 124. Each cassette includes a sample of cells to be prepared. A protocol may be selected by a user at the display 104 for preparing the sample in the cassette 124 within the instrument 100. The instrument 100 then automatically prepares the sample within the instrument according to the selected protocol.

In the embodiment illustrated in FIG. 1, the instrument can process four magazines 120, each magazine 120 having twelve cassettes 124, each cassette having a sample of cells therein at the same time according to the selected protocol. It will be appreciated, however, that fewer than forty-eight or greater than forty-eight samples can be processed at a time.

Figure 2:
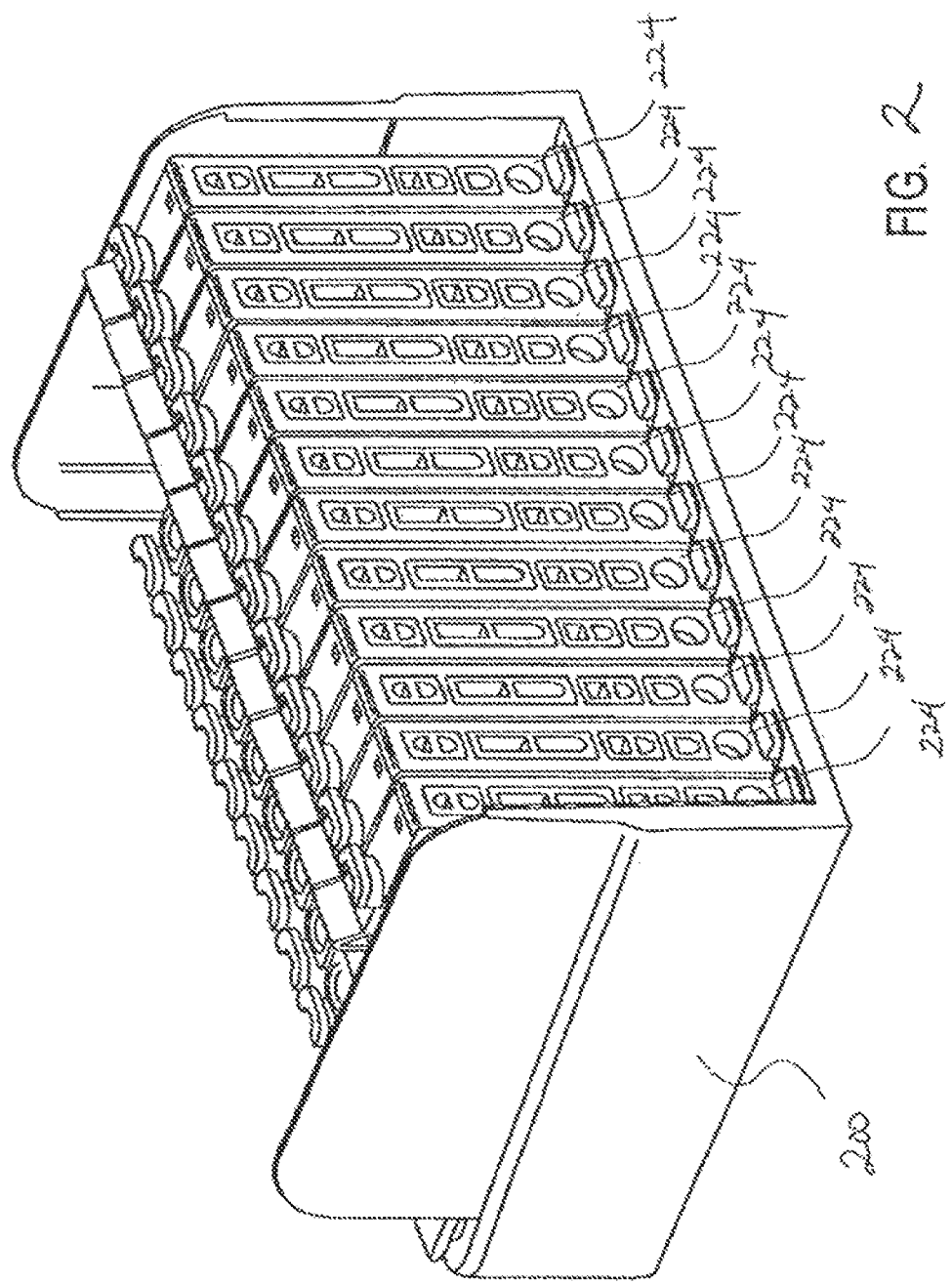
FIG. 2 is a perspective view of a magazine insertable into the instrument of FIG. 1 in accordance with one embodiment of the invention.

FIG. 2 illustrates a magazine 200 in further detail. In one embodiment, the magazine 200 is the magazine 120 of FIG. 1. In one embodiment, the magazine 200 is a rack. Several cassettes 224 (e.g., cassettes 124 from FIG. 1) are placed into the magazine 200.

Figure 3:
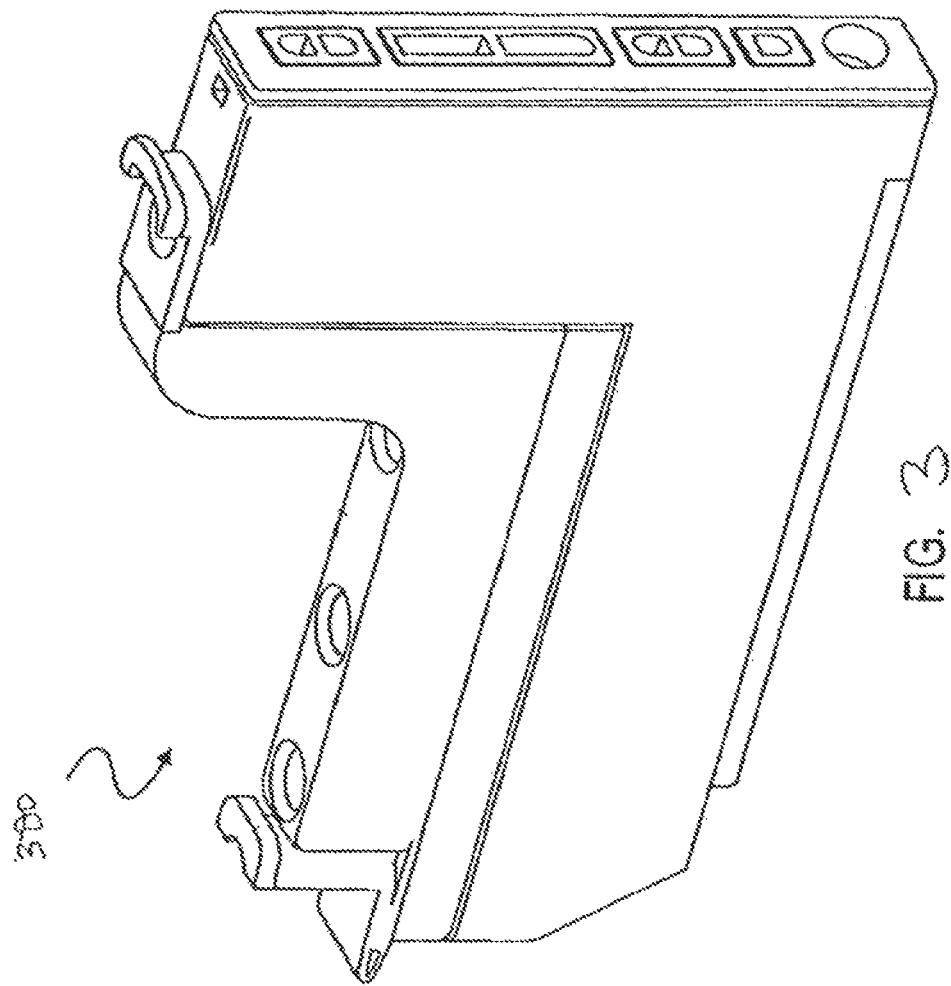
FIG. 3 is a perspective view of a cassette for preparing samples in accordance with one embodiment of the invention.

FIG. 3 illustrates a cassette 300 in further detail. In one embodiment, the cassette 300 is the cassettes 124 in FIG. 1 and/or cassettes 224 in FIG. 2. The cassette 300 can be used to prepare cell samples.

Figure 4:
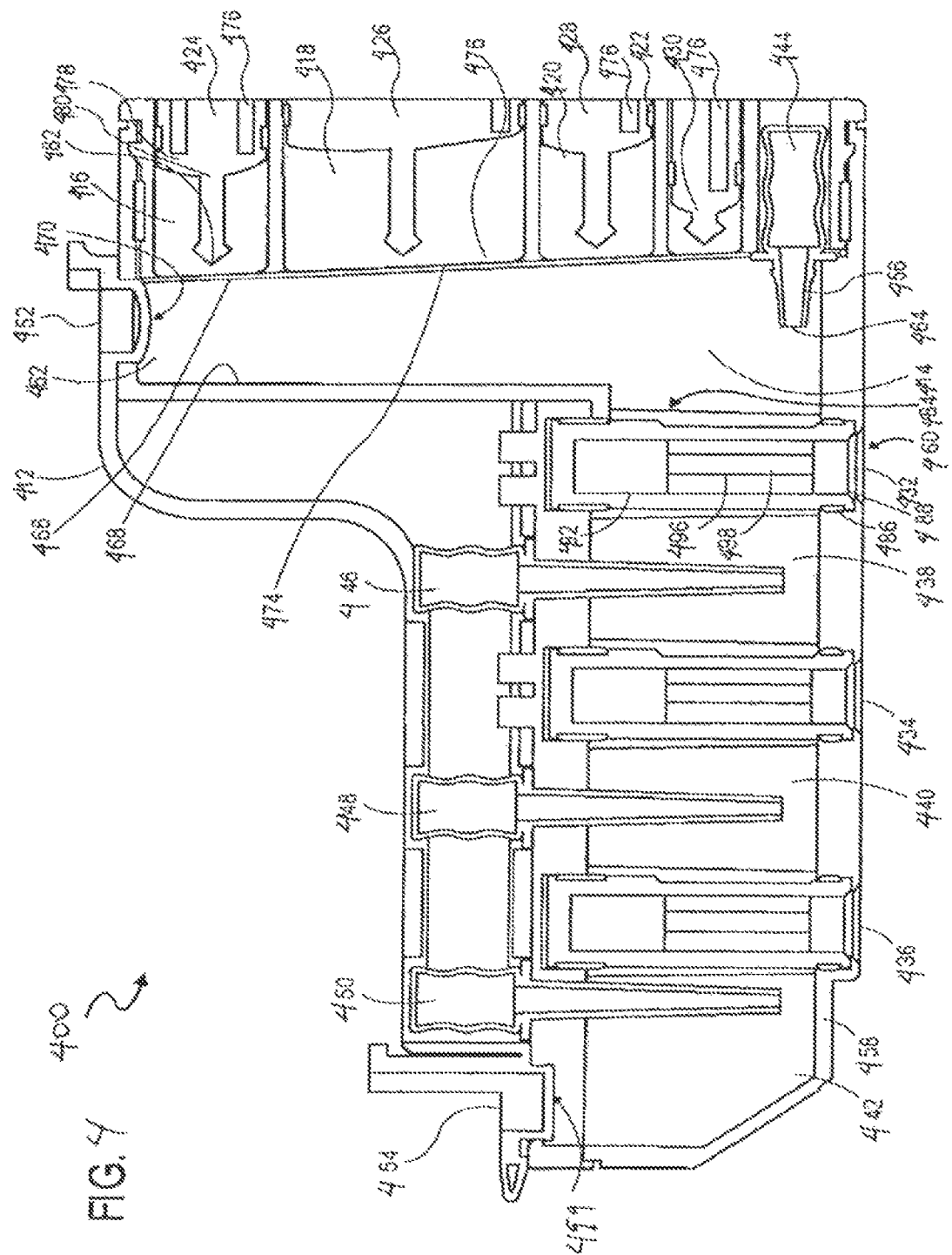
FIG. 4 is a cross-sectional side view of the cassette first preparing samples of FIG. 3 in accordance with one embodiment of the invention.

FIG. 4 is a detailed view of the cassette of FIG. 3. The cassette 400 includes a housing 412, a mixing chamber 414, first, second, third and fourth holding chambers 416, 418, 420 and 422, first, second, third and fourth plungers 424, 426, 428 and 430, first, second, and third valves 432, 434 and 436, first and second washing chambers 438 and 440, an elution chamber 442, first, second, third and fourth pumps 444, 446, 448 and 450, first and second lids 452 and 454, first and second heating elements 456 and 458 and a magnetic 460. Each of the chambers 414, 416, 418, 420, 422, 438, 440 and 442, plungers 424, 426, 428 and 430, valves 432, 434, 436, pumps 444, 446, 448 and 450, and heating elements 456 and 458 are enclosed within the housing 412. The lids 452 and 454 are movably attached to the housing 412. The magnet 460 is removably positionable in the first valve 432, second valve 434 and third valve 436.

The mixing chamber 414 has a top surface 462, a bottom surface 464 and opposing side surfaces 466, 468. The top surface 462 of the mixing chamber 414 includes an opening 470 therein.

The first lid 452 is configured to provide access to the opening 470 in the top surface 460 of the mixing chamber 414. The first lid 452 and the opening 470 are coaxial. The first lid 452 is shown being movably attached to the housing 412, such that when the lid 452 is open or off, the opening 470 is accessible and if the lid 452 is closed or on, the opening 470 is not accessible.

A thin film 474 forms one wall of the mixing chamber 414. The thin chamber 474 is breakable, such that the mixing chamber 414 is accessible when the thin film 474 has been broken or ruptured.

The first holding chamber 416, second holding chamber 418, third holding chamber 420 and fourth holding chamber 422 are shown located next to the mixing chamber 414 and aligned vertically with one another. Each of the holding chambers 416, 418, 420, 422 has an opening 476 next to the thin film 474 of the mixing chamber 414.

The cassette 400 further includes magnetic iron particles in the form of magnetic beads in the first holding chamber 416. The cassette 400 further includes a binding solution in the second holding chamber 418. The cassette 400 further includes a lysis solution in the third holding chamber 420. The cassette 400 further includes a proteinase K (PK) solution in the fourth holding chamber 422. The magnetic iron particles (in the form of magnetic beads), lysis solution, binding solution, and proteinase K (PK) can also be provided in any chamber of the cassette 400 based on desired protocol.

The first, second, third and fourth plungers 424, 426, 428 and 430 are located in the first, second, third and fourth holding chambers 416, 418, 420 and 422, respectively.

Each of the plungers 416, 418, 420, 422 includes a base 478, a shaft 480 and a piercing element 482. The shaft 480 extends from the base 478. The piercing element 482 is at the end of the shall 480 opposing the base 478 and is pointed. The piercing element 482 is configured to break or rupture the thin film 474 of the mixing chamber 414.

The first pump 444 is a bellows pump having a pumping portion and a nozzle portion. The nozzle portion of the first pump 444 is located inside the mixing chamber 414. The pumping portion of the first pump 444 is located outside the mixing chamber, such that the pumping portion is actuatable.

A heating element 456 is provided at the bottom surface 464 of the mixing chamber 414 for heating the contents of the mixing chamber 414. The heating element 456 may be a variable heating element.

The opposing side surface 468 of the mixing chamber 414 also includes an opening 484. A first valve 432 is provided between the opening 484 in the side 468 of the mixing, chamber 414 and the first washing chamber 438.

The first valve 432 has a first stationary piece 486 and a second moveable piece 488, the second piece 488 being moveable relative to the first piece 486. The first stationary piece 486 includes a first opening 490 and a second opening 492 and has a surface 494. The second piece 488 has an opening 495 therein for receiving the magnet 460. The second piece 488 has a surface 496 with a cavity 498 therein. The magnet 460 is shaped to correspond to the opening 495 in the second piece 488. The magnet 460 is moveable in the opening 495 of the second piece 488, and is removable from the second piece 488.

The cassette 400 includes a washing solution in the first washing chamber 438. The second pump 446 is also a bellows pump, and the nozzle portion of the second pump 446 is located in the first washing chamber 438.

The second vale 434 is provided between the first washing chamber 438 and the second washing chamber 440. The second vale 434 is structurally and functionally the same as the first vale 432, and also includes a first stationary piece 486 and a second moveable piece 488. The first stationary piece 486 includes a first opening 490 and a second opening 492 and has a surface 494. The second moveable piece has a surface 496 with a cavity 498 therein.

The cassette 400 includes a washing solution in the second washing chamber 440. The third pump 448 is also a bellows pump, and the nozzle portion of the third pump 448 is located in the second washing chamber 440.

The third valve 436 is provided between the second washing chamber 440 and the elution chamber 442. The third valve 436 is structurally and functionally the same as the first valve 432, and also includes a first stationary piece 486 and a second moveable piece 488. The first stationary piece 486 includes a first opening 490 and a second opening 492 and has a surface 494. The second moveable piece has a surface 496 with a cavity 498 therein.

The cassette 400 includes a washing solution in the elution chamber 442. The fourth pump 450 is also a bellows pump, and the nozzle portion of the fourth pump 450 is located in the elution chamber 442.

A heating element 458 is provided at the bottom surface of the elusion chamber 442 for heating the contents of the elution chamber 442. The heating element 458 may be a variable heating element.

The elution chamber 442 includes an opening 499 at its top surface for accessing the contents of the elution chamber 442.

The second lid 442 is configured to provide access to the opening 499 in the top surface of the elution chamber 442. The second lid 454 is coaxial with the opening 499. The second lid 454 is shown being movably attached to the housing 412, such that when the lid 454 is open or off, the opening 499 is accessible and if the lid 454 is closed or on, the opening 499 is not accessible.

In use, the first lid 452 is removed to provide access to the opening 470 of the mixing chamber 414. A sample of cells is placed into the cassette 400 and, in particular, into the mixing chamber 414. The cells in the sample include nucleic acid.

The PK solution is then added to the sample. The PK solution is added by moving the plunger 430 in the fourth holding chamber 422. A force is applied to the base 478 of the plunger 430 to move the plunger 430. As the piercing element 482 of the plunger 430 advances toward the mixing chamber 414, the piercing element 482 punctures and ruptures the thin film 474. The break in the thin film 474 provides access to the mixing chamber 414. Continued motion of the plunger 430 transfers the contents (e.g., PK solution) of the first holding chamber 422 into the mixing chamber 414.

The PK solution is mixed with the sample by pumping the mixture with, for example, the first pomp 444. The PK solution breaks up/destroys the walls of the cells of the sample, creating bulk material and nucleic acid in the bulk material.

The lysis solution is then added to the sample in a manner similar to the PK solution. The lysis solution is typically a salt or detergent. The lysis solution is used to solulibize the bulk material. The lysis solution typically does not solulibize proteins.

The heating element 456 may be used to heat the lysis solution and sample. As described hereinabove, the temperature of the heating element 456 may be variable, and is selected to optimize the effectiveness of the lysis solution.

The binding solution is then added to the sample, PK solution and lysis buffer solution. The binding solution is typically hydrophobic and increases salt in the solution. The binding solution causes the nucleic acid to be magnetically charged.

The magnetic beads are then added to the solution and pumped. The magnetic beads bind to the magnetically charged nucleic acid.

The magnetic beads, together with the nucleic acid, are bound to the first valve 432. The removable positionable magnet 460 is placed in the first valve 432 and slid to a position in the first valve 432 to attract the magnetic beads, which are bound to the nucleic acid, from the mixing chamber 414 to the first valve 432.

The magnetic beads, together with the nucleic acid, are then moved from the mixing chamber 414 and received in the first washing chamber 438.

The magnet 460 is inserted into the opening 494 of the second piece 488. The magnet 460 is inserted to a position corresponding to the openings 490 and 492 of the first piece 486. The magnet 460 attracts the magnetic beads from the mixing chamber 414 through the opening 490 in the first piece 486 and into the cavity 498 in the second piece 488. The second piece 488 is rotated such that the magnetic beads are sealed in the cavity 498 of the second piece 488, between surfaces of the second piece 488 and the first piece 486. The second piece 488 is rotated past the surface 494 of the first piece 486, such that the cavity 498 is accessible in the opening 492 of the first piece 486. The magnet 460 is then removed from the opening 494 in the second piece 488 to release the magnetic beads from the cavity 498 in the second piece 488.

The magnetic beads and nucleic acid are then washed with the washing solution by pumping the solution with the second pump 446. The magnetic beads, together with the nucleic acid, are then bound to the second valve 434 by inserting the magnet 460 into the second valve 434.

The magnetic beads, together with the nucleic acid, are then moved from the first washing chamber 438 to the second washing chamber 440 using the second valve 434. The second valve 434 transfers the magnetic beads and nucleic acid from the first washing chamber 438 to the second washing chamber 440.

The magnetic beads and nucleic acid are then washed with the washing solution a second time by pumping the solution with the third pump 448. The magnetic beads, together with the nucleic acid, are then bound to the third valve 436 by positioning the magnet 460 in the third valve 436.

The magnetic beads and nucleic acid are then moved from the second washing chamber 440 to the elution chamber 442. The magnetic beads and nucleic acid are transferred from the second washing chamber 440 to the elution chamber 442.

An elution buffer solution is then mixed with the magnetic beads and nucleic acid by pumping the solution with the fourth pump 450. The heating element 458 may be used to heat the elution buffer, magnetic beads and nucleic acid. The temperature may be variable and may be selected to optimize release of the nucleic acid from the magnetic beads.

The magnetic beads alone are then bound again to the third valve 436 by positioning the magnet 460 in the third valve 436.

The magnetic beads alone are then moved from the elution chamber 442 back into the second washing chamber 440, leaving the nucleic acid in the elution chamber 442. The magnetic beads are transferred from the elution chamber 442 to the second washing chamber 440.

The prepared sample of nucleic acid may be accessed from the opening 499 in the elution chamber 442. The second lid 54 is removed to provide access to the opening 499 in the elution chamber 42.

In one embodiment, a pipette or a multi-channel pipette may be used to place the sample in the cassette and/or access the sample or a plurality of samples in the cassette(s).

It will be appreciated that the cassette may vary from that illustrated and described above. For example, seals may be provided in the cassette as need. In another example, although the cassette 400 has been described as having a mixing chamber 414, two washing chambers 438 and 440 and an elution chamber 442, it is envisioned that only one washing chamber or no washing chamber may alternatively be provided.

In another example, the valves may have a different arrangement than that described above. In another example, although the cassette has been described as using a single removable magnet 460, it is envisioned that each valve may include a positionable magnet, such that the magnet does not need to be removed. The magnet 460 may be rotatable, and used to rotate the second piece of the valves. Alternatively, the magnet may only slide inside of each of the valves, and the second piece is rotated independent of the magnet. It is envisioned that a cassette 400 that does not use valves as described herein may be used to transfer the magnetic particles from the mixing chamber to the elution chamber. In such an embodiment, a slideable magnet may be provided to transfer the magnetic particles from one chamber to the next.

It is envisioned that the housing 412 may be transparent, such that the procedure can be viewed. In one embodiment the thin film 474 is a lamination. In one embodiment, the lids 452 and 454 may be screw-top lids. In one embodiment, the lids 452, 454 include a hydrophobic membrane, which allows gasses to vent through the lid, but does not allow the liquids to escape the cassette 400. In one embodiment, pump 450 is insertable into opening 499. In one embodiment, pump 450 can also be used as a pipette to remove the sample from the cassette 400. It is also envisioned that the mixing chamber 414 may be provided without a puncturable thin film 474. In such an embodiment, the plungers 424, 426, 428 and 430 would not need a piercing element 482. Instead, the plungers 424, 426, 428 and 430 would have a sealing element to prevent leakage of the contents of the holding chamber 416, 418, 420 and 422, associated with each plunger 424, 426, 428 and 430, respectively, until the plunger was moved.

In one embodiment, a total of about 200 µL sample is placed into the cassette. The sample is mixed with a total of about 50 µL of the PK solution by pumping the mixture of the sample and PK solution for about one minute. A total of about 200 µL of the lysis solution is added to the sample and PK solution, and the solutions are pumped for about one minute to mix the solutions. The mixture is then heated at about 60° C. for about ten minutes, and the mixture is allowed to cool for about 5 minutes. The mixture is further pumped while it cools. A total of about 500 µL of binding solution is added to the mixture. The solutions are pumped for about one minute. The magnetic beads are added to the solution and pumped for about two minutes. The magnetic beads are transferred and washed as described above. A total of about 700 µL of washing solution is provided in each of the washing chambers. A total of about 200 µL of elution solution is provided in the elution chamber. The magnetic beads are mixed with the elution solution by pumping the mixture for about one minute. The mixture is then heated at about 90° C. for about two minutes. The process continues as previously described. It will be appreciated that the amounts, times and temperatures described above may vary from that described above.

Although the cassette 400 has been described as using a PK solution, lysis solution, binding solution and magnetic beads to release the nucleic acid and magnetic beads, it is envisioned that it may be possible to practice the invention without using each of the above solutions. In addition, although the solution was described as using a PK solution to break up the cells, it is envisioned that any enzyme which causes cells to break up to release nucleic acid may be used with the invention. Furthermore, it will be appreciated that additional solutions may be provided, as needed, to prepare the sample. One of skill in the art will also understand that the cassette 400 may be modified to have fewer holding chambers if fewer solutions are used or additional holding chambers if additional solutions are used.

Figure 5:
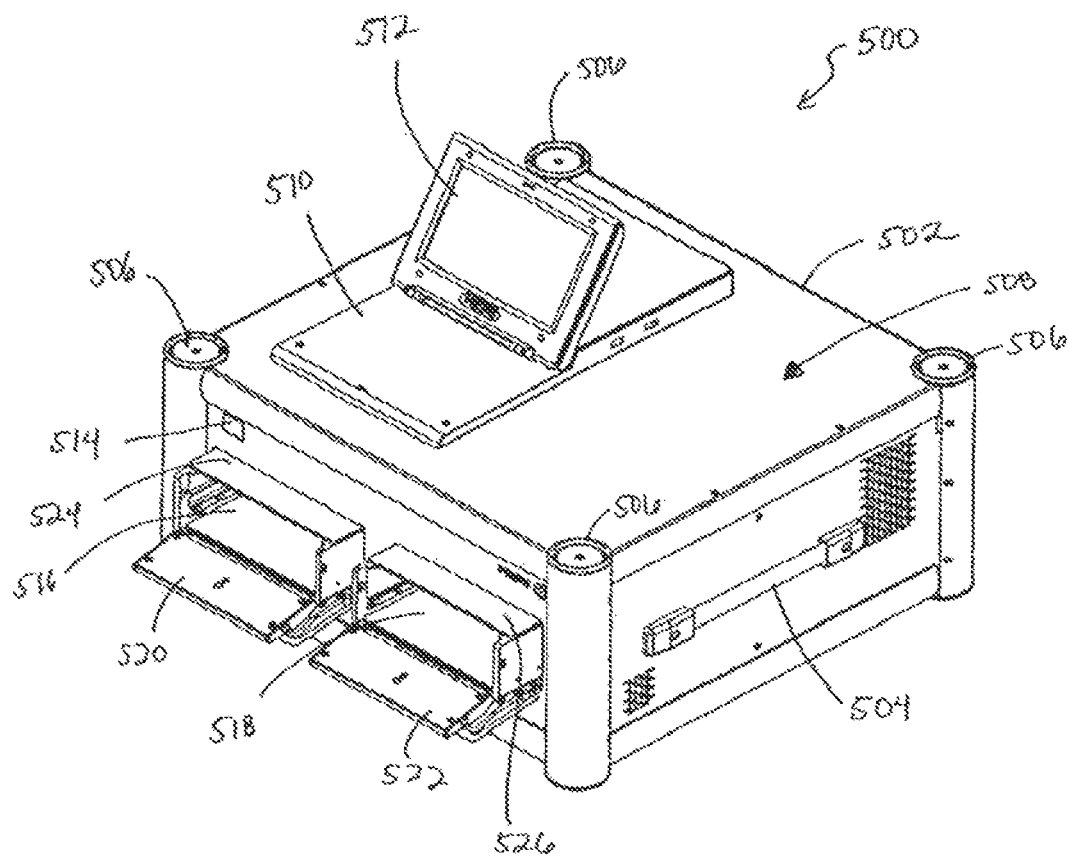
FIG. 5 is a perspective view of an instrument for a cassette for sample preparation in accordance with one embodiment of the invention.

FIG. 5 illustrates another embodiment of an instrument 500 in accordance with one embodiment of the invention. It will be appreciated that the magazine and cassettes described herein with reference to FIGS. 2-4 can be used with the instrument 500. The instrument 500 allows for parallel processing of one or more samples within a closed, sterile environment.

Instrument 500 includes an enclosure 502, an instrument handle 504, stackable holders 506, an instrument module 508, a computer module 510, a touch panel display 512, an instrument run time indicator 514, first and second automatic eject/load trays 516, 518, first and second tray doors 520, 522, and first and second tray safety guards 524, 526.

The instrument module 508 is within the enclosure 502 and is configured to perform the protocol selected to prepare the sample. The protocol is selected by the user using the touch screen display 512. In one embodiment, the display 512 is a touch screen display. For example, the display 512 may be, for example, a 7" to 12" touch screen LCD display. The user's selection at the display 512 is communicated to the computer module 510 which communicates with the instrument module 508 via a controller area network, bus (CAN-BUS) to coordinate processing within the instrument 500.

The stackable holders 506 enable multiple instruments 500 to be stacked on top of one another such that even more samples can be processed at any given time. In one embodiment, one computer module 510 and display 512 may be provided to control processing within multiple stacked instruments.

The first and second automatic eject/load trays 516, 518 are configured to receive a magazine (e.g., magazine 200) having one or more cassettes therein (e.g., cassette 400). The magazines are automatically loaded into the instrument 500 by the automatic eject/load trays 516, 518. The first and second cassette doors 520, 522 are closed and engage with the first and second tray safety guards 524, 526 to secure the magazine and cassettes within the enclosure 502 of the instrument 500 for preparation of the sample. It will be appreciated that in alternative embodiments the trays 516, 518 and/or doors 520, 522 may be manually opened and closed.

In, embodiment, the instrument run time indicator 514 is an LED or other exemplary light source. The instrument run time indicator 514 is illuminated to indicate to a user about the instrument ID and run status. In one embodiment, the computer module 510 provides an indication to the instrument run time indicator 514 to illuminate the communication status between the controller and the instrument.

Figure 6A:
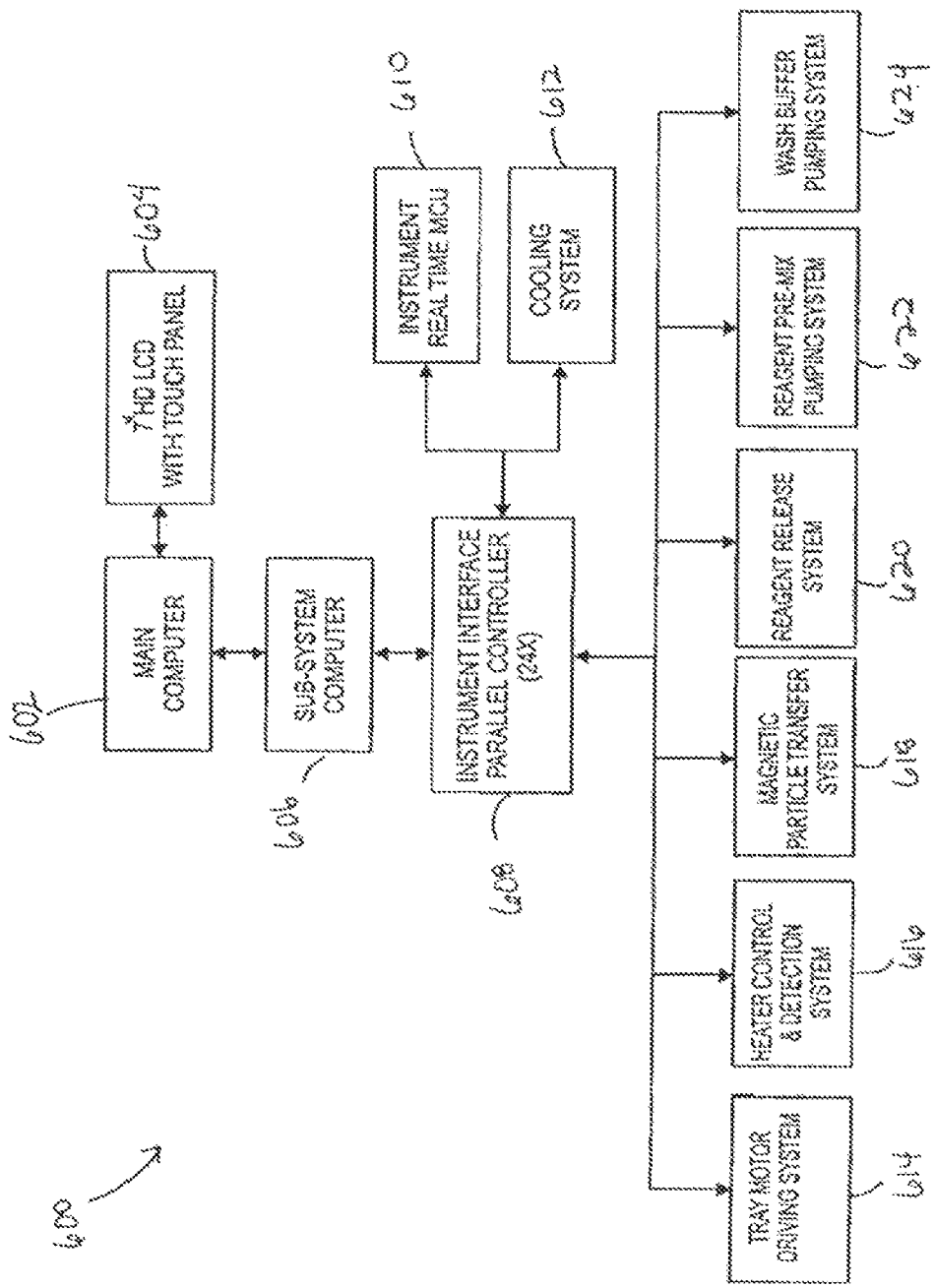
FIG. 6A is a block diagram of the system of the instrument of FIG. 5 in accordance with one embodiment of the invention.

FIG. 6A is a block diagram of the system components 600 of the instrument 500. The system components 600 include, a main computer 602, a display panel 604, a sub-system computer 606, an instrument interface parallel controller 608, an instrument real time microcontroller unit (MCU) 610, a cooling system 612, a tray motor driving system 614, a heater control and detection system 616, a magnetic particle transfer system 618, a reagent release system 620, a reagent pre-mix pumping system 622 and a wash buffer pumping system 624.

Each of the cooling system 612, tray motor driving system 614, heater control and detection system 616, magnetic particle transfer system 618, reagent release system 620, reagent pre-mix pumping system 622 and wash buffer pumping system 624 communicate with the instrument interface parallel controller 608. In one embodiment, the instrument interlace parallel controller is configured to control the subsystem 612-624 such that up to twenty-four samples can be prepared at a given time. It will be appreciated, however, that the instrument can be configured to prepare fewer than or greater than twenty-four samples. It will be appreciated that the system components 600 communicate with one another to enable parallel processing of the sample(s) within the instrument 500.

The instrument interface parallel controller 608 also communicates with the instrument real time MCU 610, the cooling system 612 and the sub-system computer 606. The sub-system computer 606 communicates with the main computer 602. The main computer 602 communicates with the touch screen display panel 604.

In one embodiment, the main computer 602, sub-system computer 606, and/or the instrument interface parallel controller 608 are a digital processing system. The digital processing system may include a microprocessor, an ASIC (application specific integrated circuit), FPGA (field-programmable gate array), DSP (digital signal processor), or the like. In one embodiment, the display panel 604 is a 7" high definition (HD) liquid crystal display (LCD) with a touch panel. The display panel 604 is on an external surface of the instrument 500 such that the user can interact with the display panel 604. The main computer 602 may be a stand alone system that includes the computer module 510 and display 512. The sub-system computer 606 and instrument interface parallel controller 608 are within the enclosure 502 of the instrument 500. As described above with reference to FIG. 5, the user can select a protocol for processing the sample(s) with the display panel 604. The display panel 604 communicates the user selection to the main computer 602, sub-system computer 606 and/or parallel controller 608 to perform the protocol using the tray motor driving system 614, heater control and detection system 616, magnetic particle transfer system 618, reagent release system 620, reagent pre-mix pumping system 622 and wash butter pumping system 624.

In one embodiment, the tray motor driving system 614 is configured to control the automatic load/eject trays 516, 518 (from FIG. 5) and cassette doors 520, 522 to automatically load the cassettes (e.g., cassette 400) for processing and eject the cassettes when processing of the sample is completed.

In one embodiment, the heater control and detection system 616 is configured to control and detect the temperature of the cassette or cassettes. The heater control and defection system may also control the heaters within the cassette to perform a close loop temperature ramping and detection. Alternatively or in addition to controlling the heaters within the cassette, the heater control and detection system 614 may include heaters that are configured as a programmable temperature controller to heat the contents of the cassette to a predefined temperature, as needed, according to the selected protocol.

In one embodiment, the magnetic particle transfer system 618 is configured to transfer magnetic particles within the cassette (e.g., cassette 400) according to the selected protocol. In one embodiment, the magnetic particle transfer system 618 manipulates the valves 432, 434, 436 to transfer the magnetic particles as described above with reference to FIG. 4.

In one embodiment, the reagent release system 620 is configured to release the reagents within the cassette. For example, the reagent release system is configured to release the PK solution, lysis solution, binding solution and magnetic beads from their respective holding chambers 416, 418, 420 and 422 and into the mixing chamber 414, as described above with reference to FIG. 4.

In one embodiment, the reagent pre-mix pumping system 622 is configured to mix the reagents in the mixing chamber 414 as described above with reference to FIG. 4.

In one embodiment, the wash buffer pumping system 624 is configured to pump the washing solution in the cassette, as described above with reference to FIG. 4. For example, the wash buffer pumping system 624 may be configured to actuate the pumps 446, 448, 450 in the wash chambers 438, 440 and elution chamber 442.

Figure 6B:
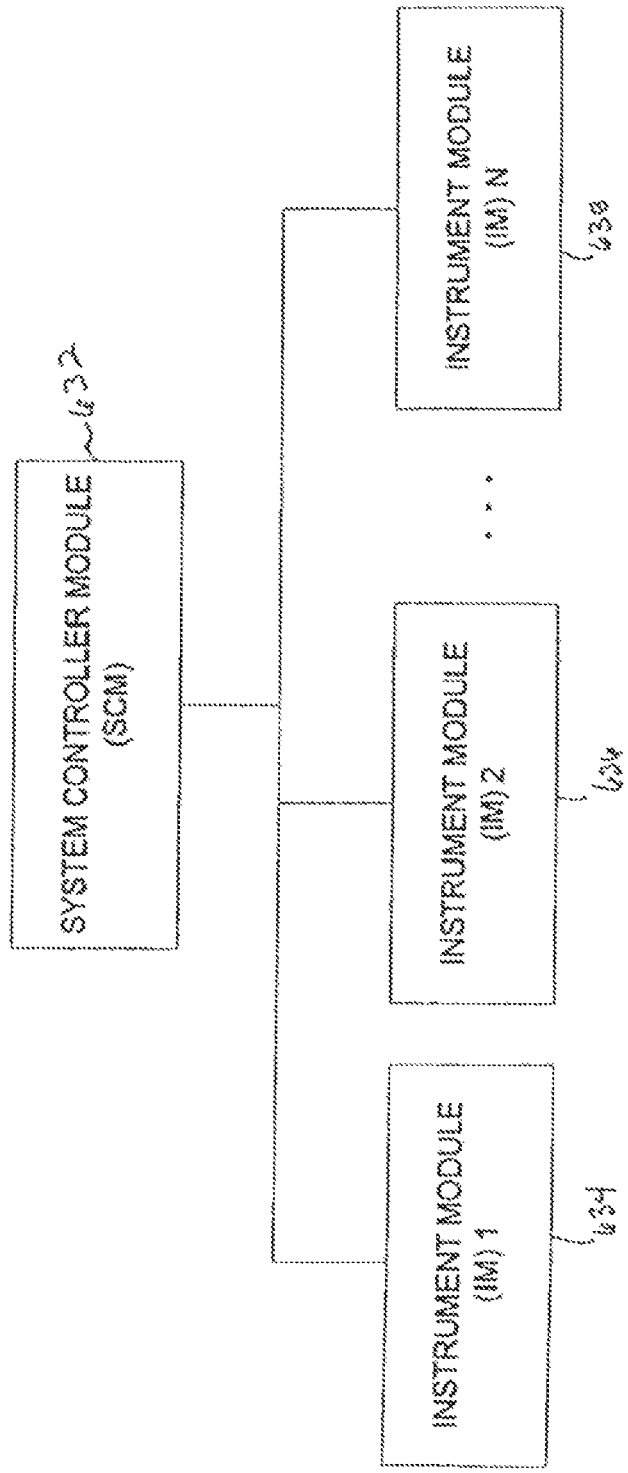
FIG. 6B is a top level digital block diagram of the system controller of the instrument of FIG. 5 in accordance with one embodiment of the invention.

FIG. 6B illustrates a block diagram of a digital system 630 in accordance with one embodiment of the invention. The illustrated digital system 630 includes a system controller module (SCM) 632, a first instrument module (IM) 1 634, a second instrument modulo (IM) 2 636 and a nth instrument module (IM) N 638. The SCM 632 controls each of the IM 1 634, IM 2 636 and up to an nth IM N 638. It will be appreciated that the SCM 632 may control any number of IMs as represented by N. Thus, N may be any number from 0 up to 100 or even more.

Figure 6C:
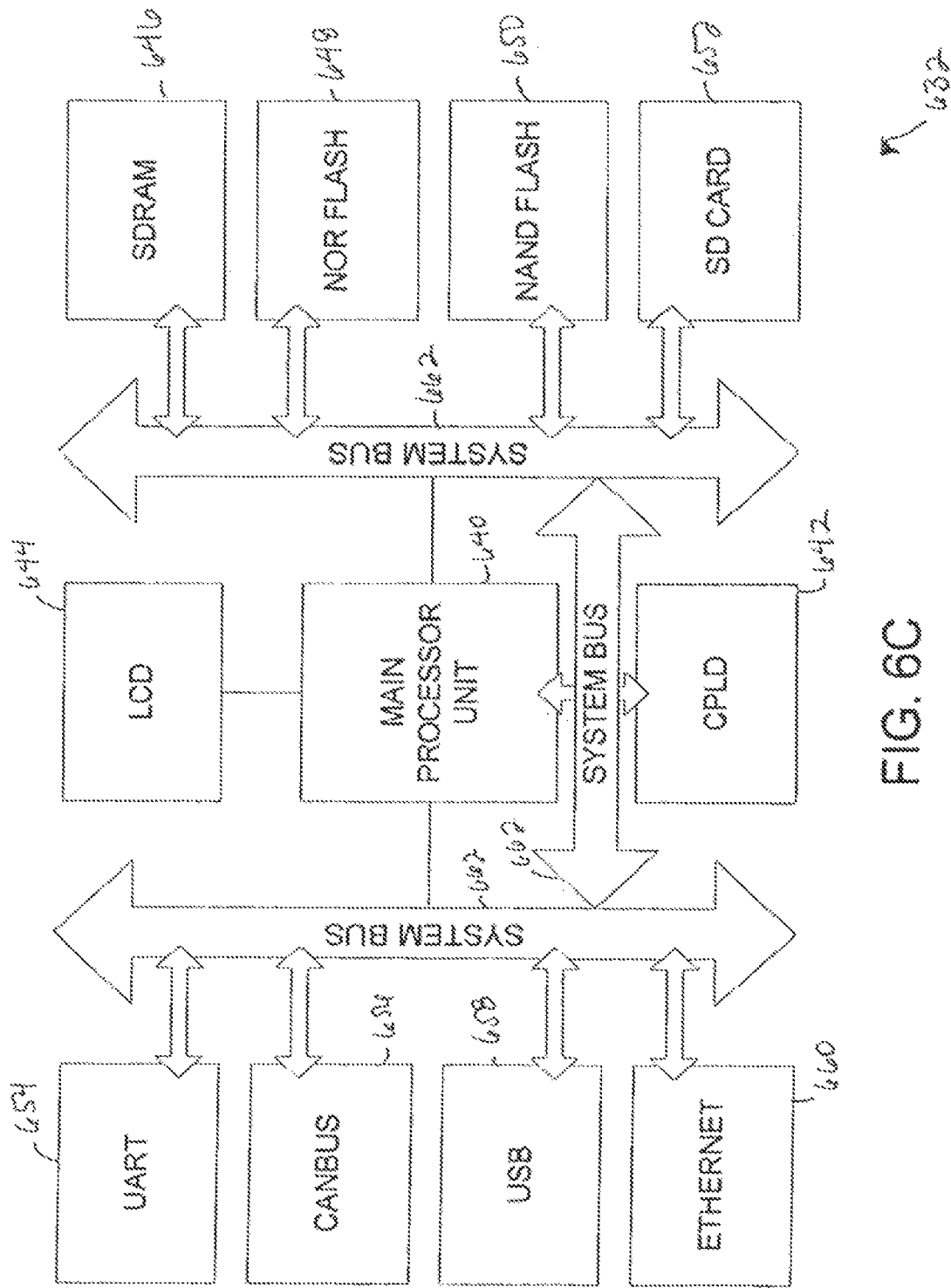
FIG. 6C is a digital processing block diagram of the system controller of the instrument of FIG. 5 in accordance with one embodiment of the invention.

FIG. 6C is a block diagram illustrating the system controller module 632 of FIG. 6B in further detail. The system controller module 632 includes a main processor unit 640, a Complex Programmable Logic Device (CPLD) 642, a Liquid Crystal Display (LCD) 644, a Synchronous Dynamic Random Access Memory (SDRAM) 646, a NOR flash 648, a NAND flash 650, a Storage Device (SD) card 652, a Universal Asynchronous Receiver-Transmitter (UART) 654, a CAN-BUS 656, a Universal Serial bus (USB) 658, an Ethernet 660 and a system bus 662 to couple each of the components 640-662.

The bus 662 or other internal communication means is for communicating information, and the main processor unit 640 is coupled, to the bus 662 for processing information. SDRAM 646, NOR flash 648, NAND flash 650, and SD card 652 (referred to as memory) are for storing information and instructions to be executed by the main processor unit 640, for storing temporary variables or other intermediate information during execution of instructions by main processor unit 640, for storing static information and instructions for main processor unit 640, and the like.

The system may further be coupled to a display device, such as a cathode ray tube (CRT) or a liquid crystal display (LCD) 644, coupled to bus 662 through bus 662 for displaying information to a computer user. An alphanumeric input device 675, including alphanumeric and other keys, may also be coupled to bus 662 through bus 662 for communicating information and command selections to the main processor unit 640. An additional user input device is cursor control device, such as a mouse, a trackball, stylus, or cursor direction keys coupled to bus 662 through bus 662 for communicating direction information and command selections to main processor unit 640, and for controlling cursor movement on display device 644.

Another device, which may optionally be coupled to computer system, is a communication device, such as UART 654, CANBUS 656, USB 658, and Ethernet 660, for accessing other nodes of a distributed system via a network. The communication device may include any of a number of commercially available networking peripheral devices such as those used for coupling to an Ethernet, token ring, Internet, control area network (CAN), wide area network (WAN), and wireless network (WIFI). The communication device may further be a null-modem connection via UART, or any other mechanism that provides connectivity between the computer system and the outside world, or any other mechanism that provides connectivity between the controller computer system and instrument modules. Note that any or all of the components of this system illustrated in FIG. 6C and associated hardware may be used in various embodiments of the present invention.

It will be appreciated by those of ordinary skill in the art that any configuration of the system may be used for various purposes according to the particular implementation. The control logic or software implementing the present invention can be stored in SDRAM 646, NOR Flash 648, NAND flash 650, SD card 652, FPGA, CPLD or other storage medium locally or remotely accessible to main processor unit 640.

It will be apparent to those of ordinary skill in the art that the system, method, and process described herein can be implemented as software stored in memory and executed by main processor unit 640. This control logic or software may also be resident on an article of manufacture comprising a computer readable medium having computer readable program code embodied therein and being readable by the storage device and for causing the main processor unit 640 to operate in accordance with the methods and teachings herein.

The present invention may also be embodied in a handheld or portable device containing a subset of the computer hardware components described above. For example, the handheld device may be configured to contain only the bus 662, the main processor unit 640, and SDRAM 646. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a main processor unit 640, SDRAM 646 and bus 662, and only rudimentary communications mechanisms, such as a small touch-screen that permits the user to communicate in a basic manner with the device. In general, the more special-purpose the device is, the fewer of the elements need to be presented for the device to function. In some devices, communications with the riser may be through a touch-based screen, USB devices, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, electrical, optical, acoustical or other forms of propagated signals (e.g. carrier waves, infrared signals, digital signals, etc.).

Figure 6D:
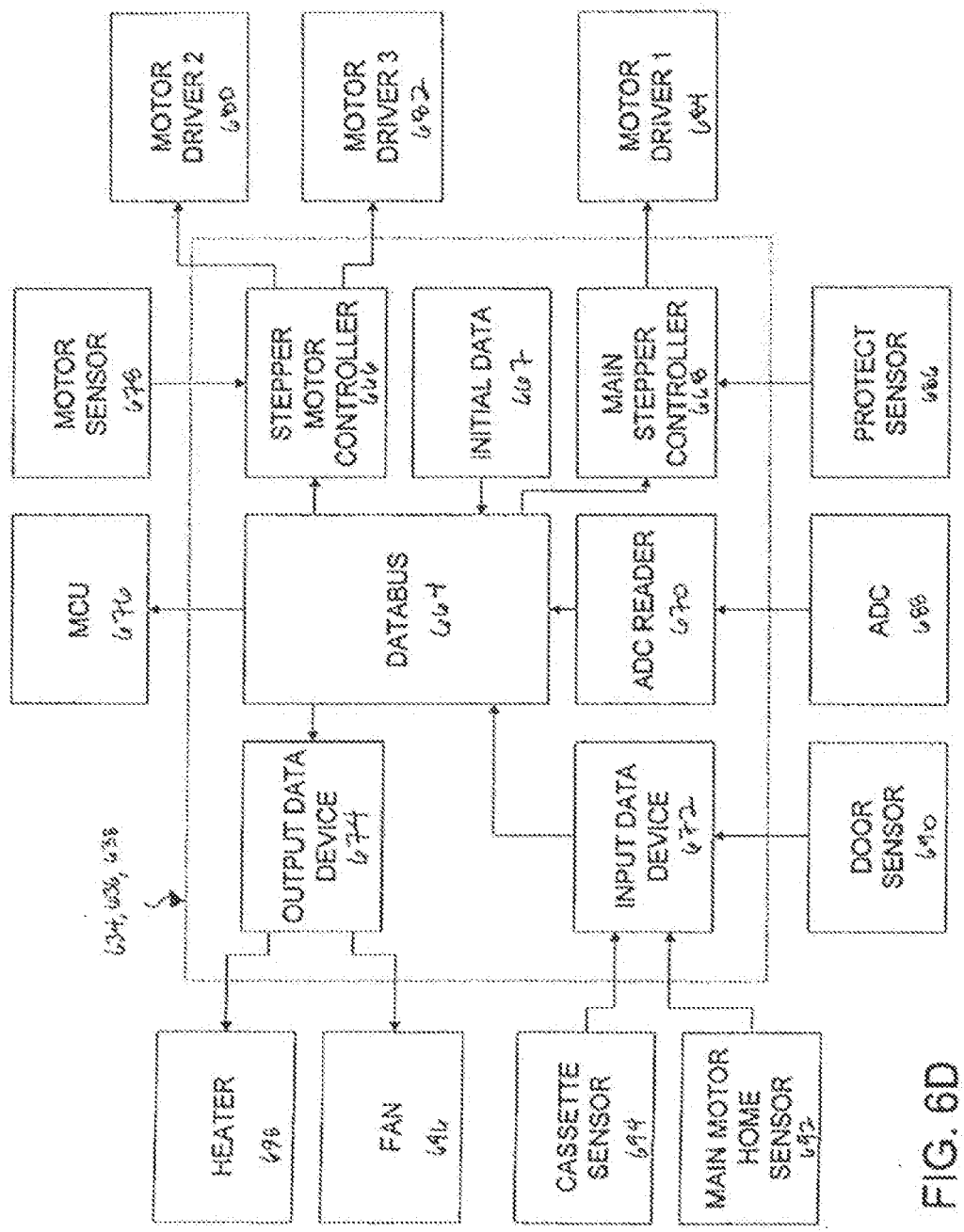
FIG. 6D is an Instrument Module (IM) block diagram of FIG. 5 in accordance with one embodiment of the invention.

FIG. 6D is a block diagram illustrating the instrument modules 634, 636, 638 of FIG. 6B in further detail. The instrument modules 634, 636, 638 include a databus 664, a stepper motor controller 666, initial data 667, a main stopper controller 668, an ADC reader 670, an input data device 672 and an output data device 674. The stepper motor controller 666, initial data 666, main stepper controller 668. Analog-to-Digital Converter (ADC) reader 670, input data device 672 and output data device 674 are each coupled to the databus 664.

In the embodiment illustrated in FIG. 6D, the instrument module is shown for the tray motor driving module of FIG. 6A. It will be appreciated that the instrument modules for the other modules of FIG. 6A will have similar components as the illustrated instrument module; however, the inputs and outputs coupled with the instrument modules may vary.

The illustrated databus 664 is also coupled with a MCU 676. The stepper motor controller 666 is also coupled with the motor sensor 678, motor driver 2 680 and motor driver 3 682. The main stepper controller 668 is also coupled with the motor driver 1 684 and protect sensor 686. The ADC reader 670 is also coupled with the ADC 688. The input data device 672 is also coupled, with the door sensor 690, main motor home sensor 692, and cassette sensor 694. The output data device 674 is also coupled with the fan 696 and the heater 698.

Figure 7:
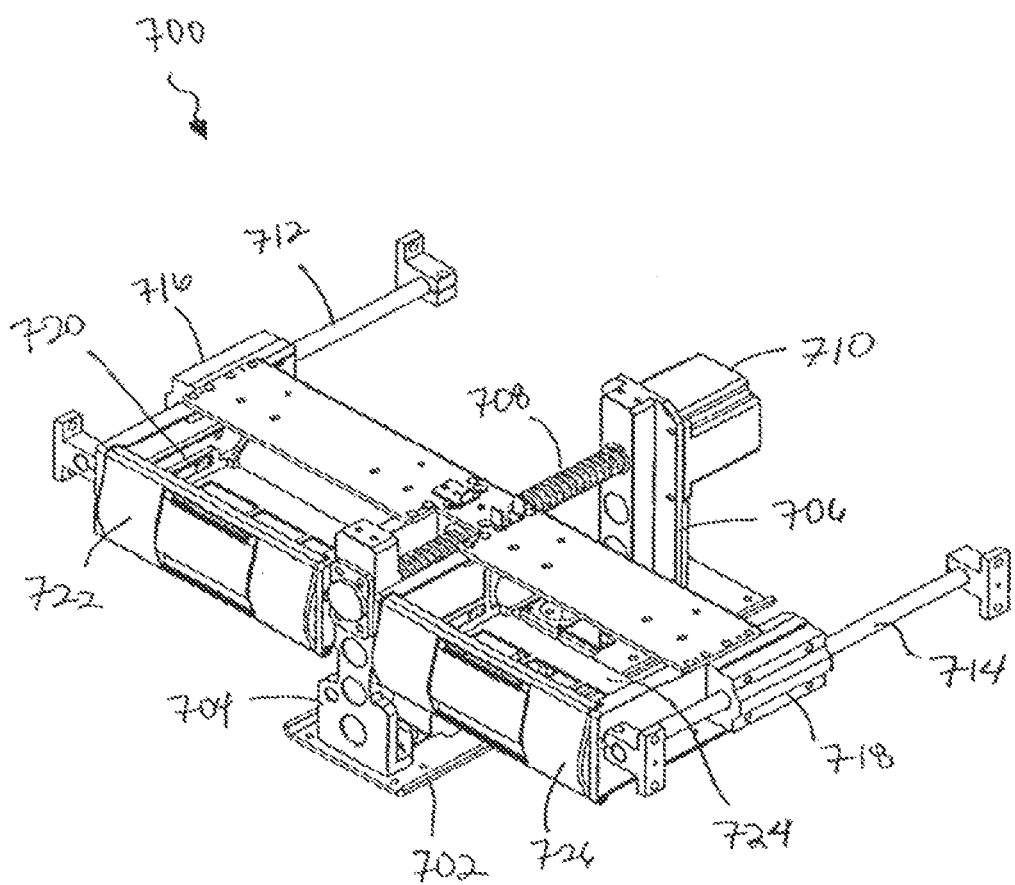
FIG. 7 is a detailed perspective view of a parallel tray driving motor assembly module in accordance with one embodiment of the invention.

FIG. 7 illustrates a tray driving motor assembly module 700. In one embodiment, the tray driving motor assembly module 700 is part of the tray motor driving system 614 of FIG. 6. In one embodiment, the tray driving motor assembly module 700 is within the instrument module 508 of the instrument 500 as described above with reference to FIG. 5.

The tray driving motor assembly module 700 includes an alignment plate 702, a first drive shaft retention block 704, a second drive shaft retention block 706, a load driving shaft 708, a main driving motor 710, a first parallel shaft 712, a second parallel shaft 714, a first parallel linear drive 716, a second parallel linear drive 718, a first load resistance tray 720, a first door 722, a second load resistance tray 724 and a second door 726.

The main drive motor 710 is coupled with the load driving shaft 708 via the retention blocks 704, 706 to automatically load and eject the rack trays 720, 724 into the instrument. The trays 720, 724 also slide along the parallel shafts 712, 714 with the main drive motor 710 and the drives 716, 718 to load and eject the racks 720, 724. The motor 710 and/or drivers 712, 714 can also be used to open and close the doors 722, 726.

FIG. 8 illustrates a reagent release and pre-mix assembly module 800. In one embodiment, the reagent release and pre-mix assembly module 800 is part of the reagent release system 620 and reagent pre-mix pumping system 622. In one embodiment, the reagent release and pre-mix assembly module 800 is within the instrument module 508 of the instrument 500 as described above with reference to FIG. 5.

The reagent release and pre-mix assembly module 800 includes a precision vertical engagement driving motor 802, a vertical drive shaft 803, a stand 804, a first plunger assembly 806, a second plunger assembly 808, a first parallel horizontal pump activation motor 810, a second parallel horizontal pump activation motor 812, first, second, third and fourth horizontal parallel linear driving shafts and bearings 814, 816, 818 and 820, and first, second, third, and fourth vertical parallel linear bearings 822, 824, 826 and 828.

In one particular embodiment, each of the plunger assemblies 806, 808 includes twelve plungers (e.g., one plunger for each cassette in the magazine). It will be appreciated that the plunger assemblies 806, 808 may have fewer than or greater than twelve plungers.

Figure 9:
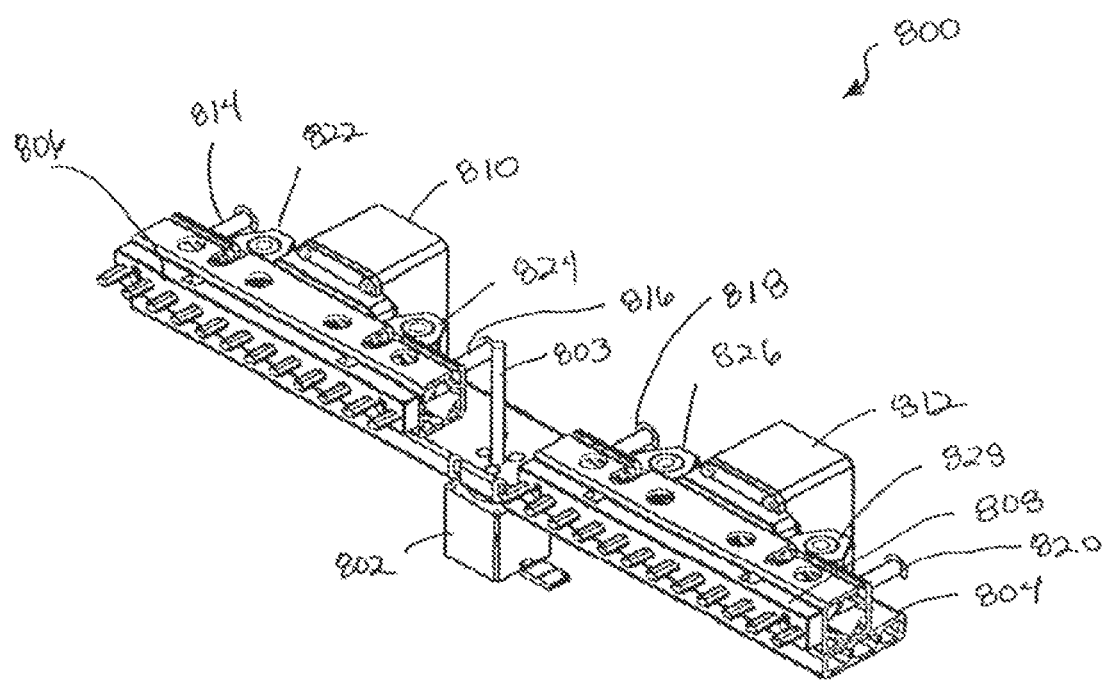
FIG. 9 is a detailed side view of the reagent release and pre-mix assembly module in accordance with one embodiment of the invention.
Figure 9:
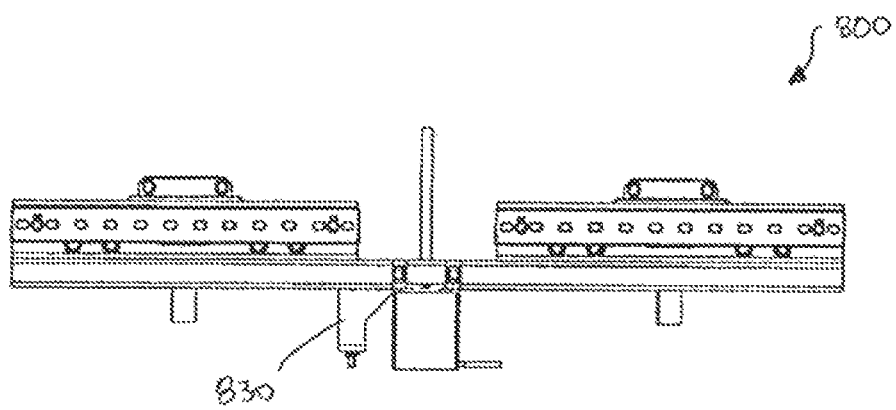

FIG. 9 is a side view of reagent release and pre-mix assembly module 800 of FIG. 8. As shown in FIG. 9, the reagent release and pre-mix assembly module 800 of FIG. 8 also includes a vertical position sensor 830.

With reference to FIGS. 8 and 9, the stand 804 is coupled with the vertical drive shaft 803, which is coupled with the vertical engagement driving motor 802 to vertically position the stand 804. The plunger assemblies 806, 808 are coupled with the stand 804 and are, thus, also vertically positioned with the stand 804 when the motor 802 is actuated. The vertical position sensor 830 is coupled with the stand 804 to sense the position of the stand 804 and/or plunger assemblies 806, 808. The vertical position sensor 830 communicates with a controller to control actuation of the motor 802. The plunger assemblies 806, 808 are also actuatable horizontally via the horizontal drive shafts and bearings 814-820, which are coupled with the horizontal motors 810, 812.

The plunger assemblies 806, 808 are actuated in a vertical direction to align the plungers 806, 808 with one of the holding chambers of the cassette 400. The plunger assemblies 800, 808 are also actuated horizontally to force the contents of the holding chambers into the mixing chamber of the cassette 400. The plunger assemblies 806, 808 are then repositioned vertically to align with another holding chamber and are similarly actuated horizontally to force the contents of the holding chamber into the mixing chamber according to the selected protocol. In one embodiment, the plunger assemblies 806, 808 are also actuated to actuate the pump 444 that mixes the contents of the mixing chamber of the cassette 400.

Figure 10:
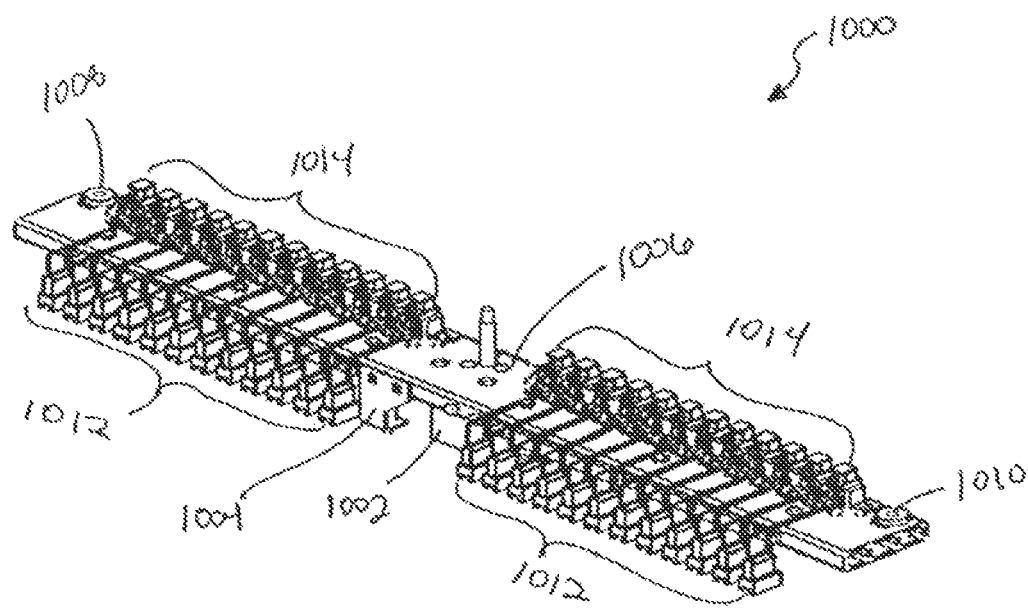
FIG. 10 is a detailed perspective view of a close-loop heater and temperature sensor assembly module in accordance with one embodiment of the invention.
Figure 11:
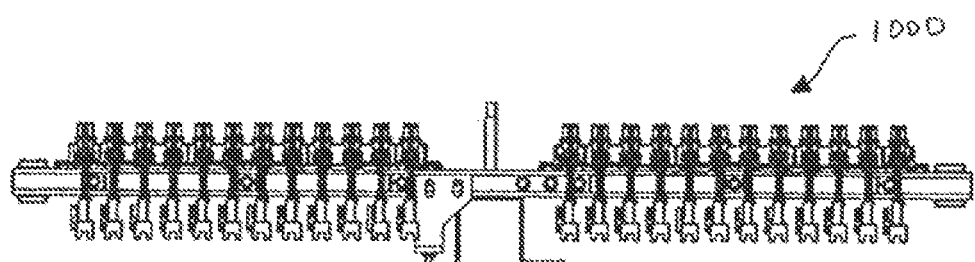
FIG. 11 is a detailed side view of the close-loop heater and temperature sensor assembly module in accordance with one embodiment of the invention.

FIGS. 10 and 11 illustrate a heater and temperature sensor assembly module 1000. In one embodiment, the heater and temperature sensor assembly module 1000 is part of the heater control and detection system 616. In one embodiment, the heater and temperature sensor assembly module 1000 is within the instrument module 508 of the instrument 500 as described above with reference to FIG. 5.

The heater and temperature sensor assembly module 1000 includes a precision vertical engagement driving motor 1002, a vertical position sensor 1004, a rack 1006, a first vertical linear bearing 1008, a second vertical linear bearing 1010, a plurality of heater and thermal sensor connectors 1012 and a plurality of individually controlled parallel heaters and thermal sensors 1014. In one embodiment, the plurality of individually controlled parallel heaters and thermal sensors 1014 are self-aligned with the plurality of heater and thermal sensor connectors 1012.

In one particular embodiment, the heater and temperature sensor assembly module 1000 includes twenty-four heater and thermal sensor connectors 1012 and twenty-four individually controlled parallel heaters and thermal sensors 1014. It will be appreciated that the heater and temperature sensor assembly module 1000 may include fewer than or greater than twenty-four connectors 1012 and/or heaters/sensors 1014.

The vertical linear bearings 1008, 1010 are coupled with the vertical engagement driving motor 1002 to vertically position the rack 1006. The plurality of heater and thermal sensor connectors 1012 and plurality of individually controlled parallel heaters and thermal sensors 1014 are coupled with respective sides of the rack 1006. The plurality of heater and thermal sensor connectors 1012 and plurality of individually controlled parallel heaters and thermal sensors 1014 are vertically positionable by vertically positioning the rack 1006. The vertical precision position sensor 1004, coupled with the rack 1006, can be used to accurately position the plurality of heater and thermal sensor connectors 1012 and plurality of individually controlled parallel heaters and thermal sensors 1014.

Figure 12:
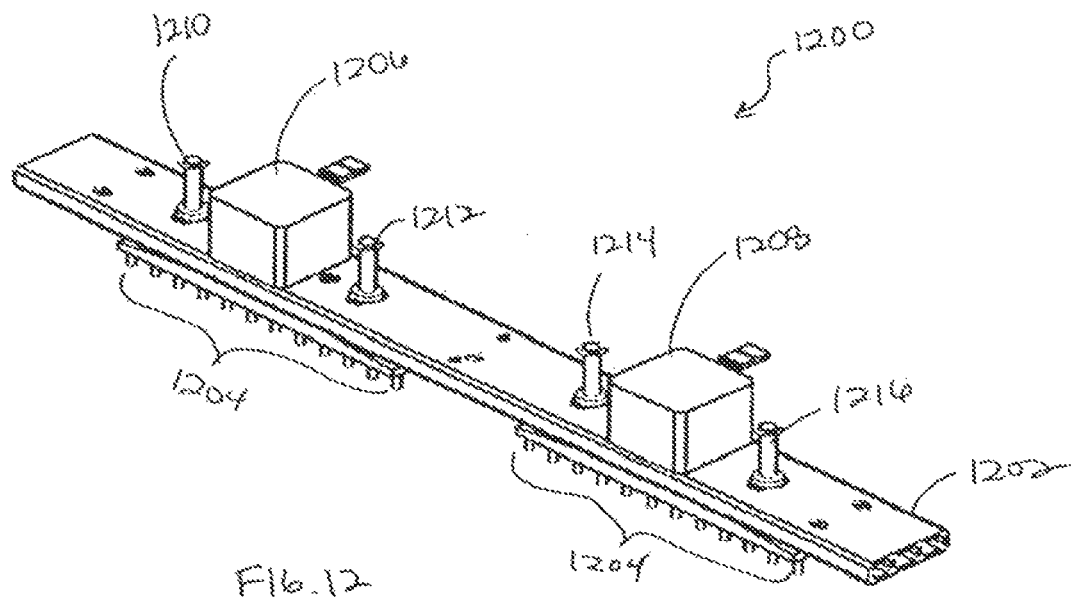
FIG. 12 is a detailed perspective view of a parallel wash buffer pumping assembly module in accordance with one embodiment of the invention.
Figure 13:
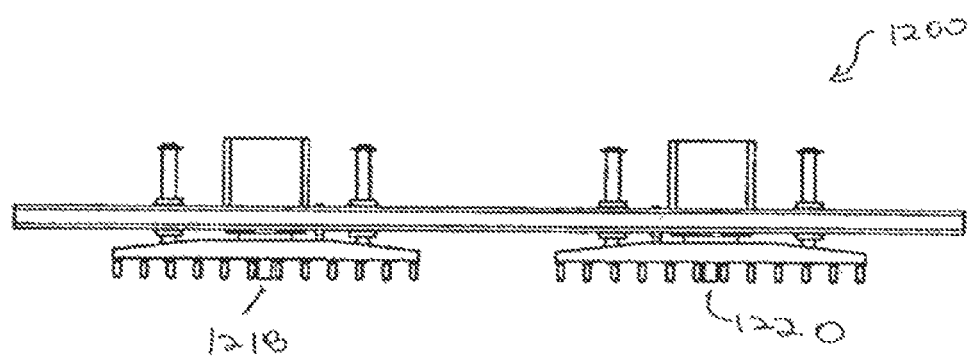
FIG. 13 is a detailed side view of the parallel wash buffer pumping assembly module in accordance with one embodiment of the invention.

FIGS. 12 and 13 illustrate a wash buffer pumping assembly module 1200. In one embodiment, the wash buffer pumping assembly module 1200 is part of the wash buffer pumping system 624. In one embodiment, the wash buffer pumping assembly module 1200 is within the instrument module 508 of the instrument 500 as described above with reference to FIG. 5.

The wash buffer pumping assembly module 1200 includes a rack 1202, a plurality of parallel vertical pump engagement plungers 1204, a first parallel vertical pump activation motor 1206, a second parallel vertical pump activation motor 1208, and first, second, third and fourth vertical parallel linear driving shafts and bearings 1210, 1212, 1214 and 1216. As shown in FIG. 13, the wash buffer pumping assembly module 1200 also includes first and second vertical precision position sensors 1218 and 1220.

The first vertical pump activation motor 1206 is coupled with the first and second vertical parallel linear driving shafts and bearings 1210, 1212 to vertically position a first set of parallel vertical pump engagement plungers 1204a. Similarly, the second vertical pump activation motor 1206 is coupled with the third and fourth vertical parallel linear driving shafts and bearings 1214, 1216 to vertically position a second set of parallel vertical pump engagement plungers 1204b.

The plungers from the vertical pump engagement plungers 1204 engage with the cassette (e.g., cassette 400) to actuate the pumps 446, 448, 450 in the wash chambers 438, 440 and elution chamber 442 according to the selected protocol.

Figure 14:
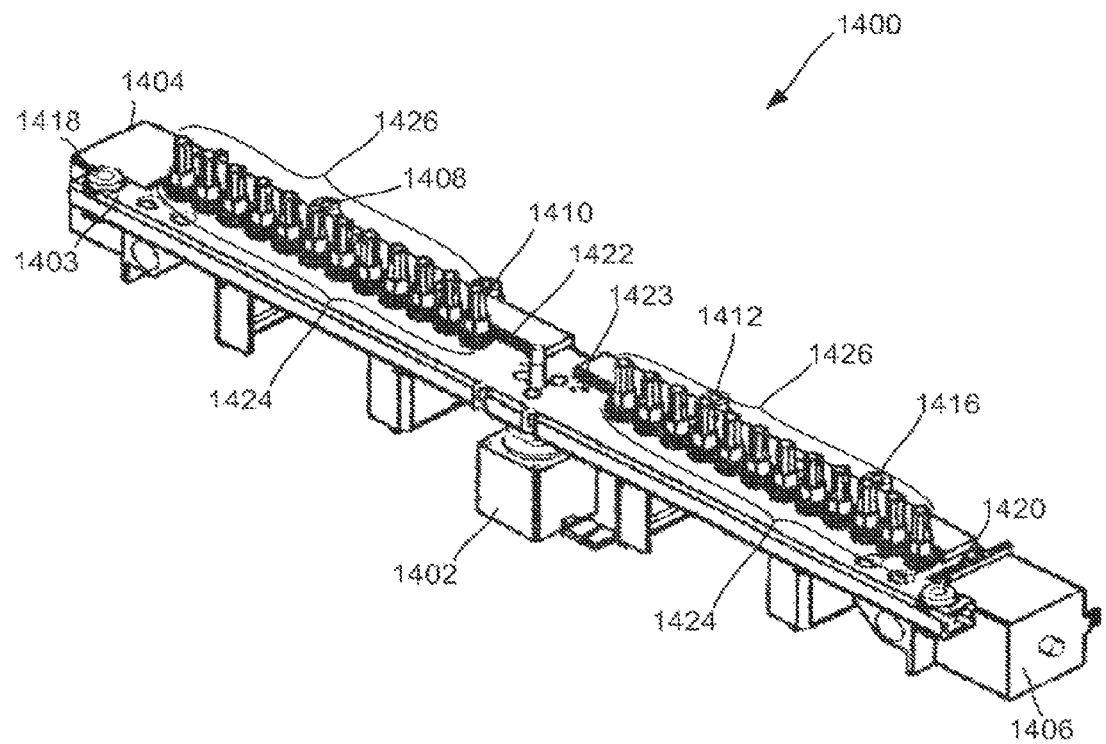
FIG. 14 is a detailed perspective view of a parallel magnetic particles transfer assembly module its accordance with one embodiment of the invention.
Figure 15:
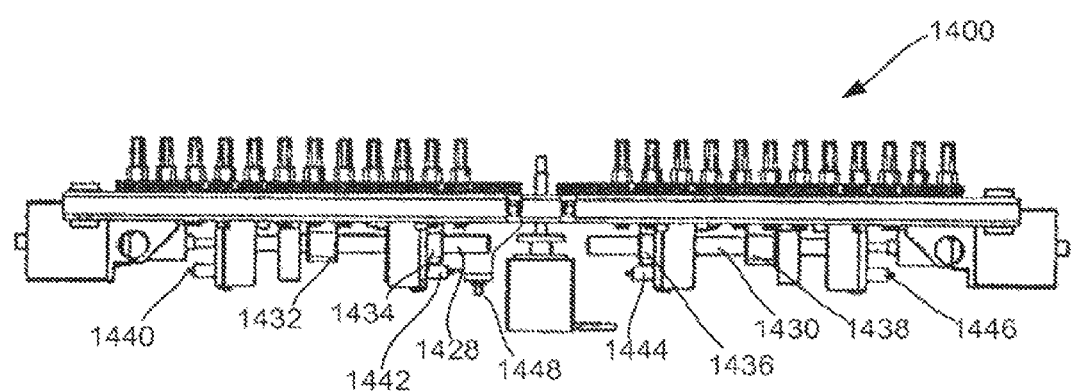
FIG. 15 is a detailed side view of the parallel magnetic particles transfer assembly module in accordance with one embodiment of the invention.

FIGS. 14 and 15 illustrate a magnetic particles transfer assembly module 1400. In one embodiment, the magnetic particles transfer assembly module 1400 is part of the magnetic particle transfer system 618. In one embodiment, the magnetic particles transfer assembly module 1400 is within the instrument module 508 of the instrument 500 as described above with reference to FIG. 5.

The magnetic particles transfer assembly module 1400 includes a rack 1402, a precision vertical engagement driving motor 1402, a first particle transfer linear motor 1404, a second particle transfer linear motor 1406, first, second, third, and fourth gear rack retention roller bearings 1408, 1410, 1412 and 1416, first and second vertical linear bearings 1418 and 1420, first and second driving gear racks 1422, 1423, a plurality of parallel precision gears 1424 and a plurality of parallel magnets and valve key shafts 1426. As shown in FIG. 15, the magnetic particles transfer assembly module 1400 also includes first and second linear driving shafts 1428 and 1430, first, second, third and fourth shaft and gear rack link blocks 1432, 1434, 1436 and 1438, first, second, third and fourth horizontal precision position sensors 1440, 1442, 1444 and 1446, and a vertical precision position sensor 1448.

In one particular embodiment, the magnetic particles transfer assembly module 1400 includes twenty-four parallel precision gears 1424 and twenty-four parallel magnets and valve key shafts 1426. It will be appreciated that the magnetic particles transfer assembly module 1400 may have fewer than or greater than twenty-four gears 1424 and magnets and key shafts 1426.

The precision vertical engagement driving motor 1402 is coupled with vertical bearings 1418, 1420 and the rack 1403 to vertically position the rack 1403. The plurality of parallel magnets and valve key shafts 1426 are positioned on the rack 1403 and are vertically portioned when the rack 1403 is vertically positioned. The vertical precision position sensor 1448 is coupled with the rack 1403 and motor 1402 to accurately position the plurality of parallel magnets and valve key shafts 1426 in the cassette (e.g., cassette 400).

The particle transfer linear motors 1404, 1405 are positioned on either end of the rack 1403 and are coupled with the linear driving shafts 1428, 1430, shaft and gear rack link blocks 1432-1438, driving gear racks 1422, gears 1424, to horizontally position and rotate the plurality of parallel magnets and valve key shafts 1426 via the gears 1424 to transfer magnetic particles as described above with reference to FIG. 4. It will be appreciated that the gears 1424 and magnets and shafts 1426 can be repositioned to transfer the particles with each valve of the cassette.

The foregoing description with attached drawings is only illustrative of possible embodiments of the described method and should only be construed as such. Other persons of ordinary skill in the art will realize that many other specific embodiments are possible that fall within the scope and spirit of the present idea. The scope of the invention is indicated by the following claims rather than by the foregoing description. Any and all modifications which come within the meaning and range of equivalency of the following claims are to be considered within their scope.

The invention claimed is:

1. An apparatus comprising:
   a rack;
   a linear drive shaft;
   a plurality of gears;
   first and second vertical linear bearings;
   a plurality of valve key shafts disposed on a first side of the rack, each of said valve key shafts comprising a magnet at an end of said valve key shafts distal to the rack;
   a linear motor coupled to the plurality of valve key shafts via the linear drive shaft and the plurality of gears, wherein the linear motor is positioned on either end of the rack;
   a vertical engagement driving motor coupled to the rack, wherein:
   the vertical engagement driving motor is configured to vertically position the rack, wherein said vertical engagement driving motor is coupled to the first and second vertical linear bearings; and
   the linear motor is configured to horizontally position and rotate the plurality of magnets and the valve key shafts via the plurality of gears.

2. The apparatus of claim 1 further comprising a vertical position sensor coupled to the rack and the vertical engagement driving motor, wherein the vertical position sensor is configured to detect a position of the plurality of valve key shafts.

3. The apparatus of claim 1 further comprising a horizontal position sensor.

4. The apparatus of claim 1 further comprising:
   a second linear drive shaft;
   a second plurality of gears;
   a plurality of second valve key shafts disposed on the first side of the rack, each of said second valve key shafts comprising a magnet at an end of each of said second valve key shafts distal to the rack;
   a second linear motor coupled to the plurality of second valve key shafts via the second linear drive shaft and the second plurality of gears.

5. The apparatus of claim 4 wherein the linear motor is positioned at a first end of the rack and the second linear motor is positioned at a second end of the rack.

6. The apparatus of claim 4 further comprising a first driving gear rack coupled to the linear motor and comprising a second driving gear rack coupled to the second linear motor.

7. The apparatus of claim 6 wherein the first driving gear rack engages each valve shaft of the plurality of valve key shafts and wherein the second driving gear rack engages each valve shaft of the plurality of second valve key shafts.

8. The apparatus of claim 1 wherein the vertical engagement driving motor is positioned between the first end of the rack and the second end of the rack, and wherein the vertical engagement driving motor is positioned proximal to a second side of the rack that is opposed to the first side of the rack.

9. The apparatus of claim 1 wherein the plurality of gears comprises parallel gears.

10. The apparatus of claim 1 wherein the apparatus is contained within an instrument configured for parallel processing of one or more samples.

11. The apparatus of claim 10 wherein the instrument is configured to perform a protocol selected to prepare a sample of the one or more samples.

12. The apparatus of claim 11 wherein the instrument comprises a touch screen display configured to allow a user to select the protocol.

13. The apparatus of claim 10 wherein the instrument comprises a magazine having one or more cassettes.

14. The apparatus of claim 13 wherein each cassette of the one or more cassettes comprises a plurality of valves.

15. The apparatus of claim 14 wherein each valve of said plurality of valves is configured to receive the magnet at the end of one of the plurality of valve key shafts.

* * * * *